United States Patent [19]
Booker et al.

[11] Patent Number: 5,282,811
[45] Date of Patent: Feb. 1, 1994

[54] TWO PART SURGICAL LIGATING CLIP, APPLICATOR AND METHOD OF USE

[75] Inventors: Robert Booker, Vandergrift, Pa.; Marc A. Cossette, Hartville, Ohio

[73] Assignee: Cook Pacemaker Corporation, Leechburg, Pa.

[21] Appl. No.: 870,482

[22] Filed: Apr. 16, 1992

[51] Int. Cl.[5] .............................................. A61B 17/00
[52] U.S. Cl. ...................... 606/157; 606/139; 606/142; 606/143; 606/151; 606/158
[58] Field of Search ............... 128/831, 843; 606/151, 606/157, 158, 220, 221, 142, 143; 227/902; 24/459, 460, 461, 462

[56] References Cited

U.S. PATENT DOCUMENTS

| | | |
|---|---|---|
| 2,245,030 | 6/1941 | Gottesfeld et al. ............... 606/158 |
| 2,779,987 | 2/1957 | Jordan ................................ 24/459 |
| 2,889,848 | 6/1959 | Redmer ............................... 24/459 |
| 3,082,867 | 3/1963 | Gelpey ................................ 24/462 |
| 3,266,711 | 8/1966 | Song .................................... 24/462 |
| 3,318,224 | 5/1967 | Bohanon ............................. 24/462 |
| 3,916,908 | 11/1975 | Leveen ............................... 606/157 |
| 4,152,920 | 5/1979 | Green . |
| 4,188,953 | 2/1980 | Klieman et al. . |
| 4,226,242 | 10/1980 | Jarvik . |
| 4,414,721 | 11/1983 | Hufnagel . |
| 4,440,170 | 4/1984 | Golden et al. . |
| 4,446,865 | 5/1984 | Jewusiak . |
| 4,450,840 | 5/1984 | Mericle et al. . |
| 4,476,865 | 10/1984 | Failla et al. . |
| 4,500,024 | 2/1985 | DiGiovanni et al. .............. 227/19 |
| 4,509,518 | 4/1985 | McGarry et al. . |
| 4,512,345 | 4/1985 | Green . |
| 4,559,675 | 12/1985 | Devenny ............................ 24/460 |
| 4,562,839 | 1/1986 | Blake, III et al. . |
| 4,569,346 | 2/1986 | Peirier . |
| 4,598,711 | 7/1986 | Deniega . |
| 4,602,629 | 7/1986 | Schnirman . |
| 4,616,650 | 10/1986 | Green et al. ....................... 606/143 |
| 4,733,666 | 3/1988 | Mercer, Jr. . |
| 4,777,949 | 10/1988 | Perlin . |
| 4,834,096 | 5/1989 | Oh et al. . |
| 4,844,066 | 7/1989 | Stein . |
| 4,950,284 | 8/1990 | Green et al. ....................... 606/216 |
| 4,971,198 | 11/1990 | Mericle . |
| 4,976,722 | 12/1990 | Failla ................................. 606/157 |
| 4,979,950 | 12/1990 | Transue et al. .................... 606/158 |
| 5,002,552 | 3/1991 | Casey ................................. 606/157 |
| 5,149,027 | 9/1992 | Weber ................................ 24/459 |

FOREIGN PATENT DOCUMENTS

| | | | |
|---|---|---|---|
| 2932652 | 2/1981 | Fed. Rep. of Germany ...... 606/151 |
| 2598905 | 11/1987 | France ............................... 606/151 |
| 2127481 | 4/1984 | United Kingdom .............. 606/158 |

Primary Examiner—Stephen C. Pellegrino
Assistant Examiner—Jeffrey A. Schmidt
Attorney, Agent, or Firm—Richard J. Godlewski

[57] ABSTRACT

A surgical clip having first and second separate pieces for ligating a vessel therebetween, an applicator for applying the clip to the vessel, and a method of use thereof. The surgical clip comprises a first tube having a longitudinal slot formed through the outer wall thereof and communicating with a passage extending therethrough for receiving a second tube into the passage of the first tube and circumferentially ligating a vessel positioned in a second channel transverse to and communicating with the first passage. Tangs or projections extend from the outer wall of the first tube about the longitudinal slot thereof and into the passage of the first tube for engaging the walls about a slot in the second tube and securably positioning the second tube in the passage of the first tube. An applicator includes a main housing having a vessel channel for positioning the first tube therein. The vessel channel also includes vessel access openings for transversely positioning a vessel through openings in the first tube outer wall. An insertion mechanism carrying a plurality of second piece tubes slides over the inserted vessel and first tube and securably positions a second tube in the passage of the first piece tube for circumferentially ligating the vessel positioned therebetween.

66 Claims, 18 Drawing Sheets

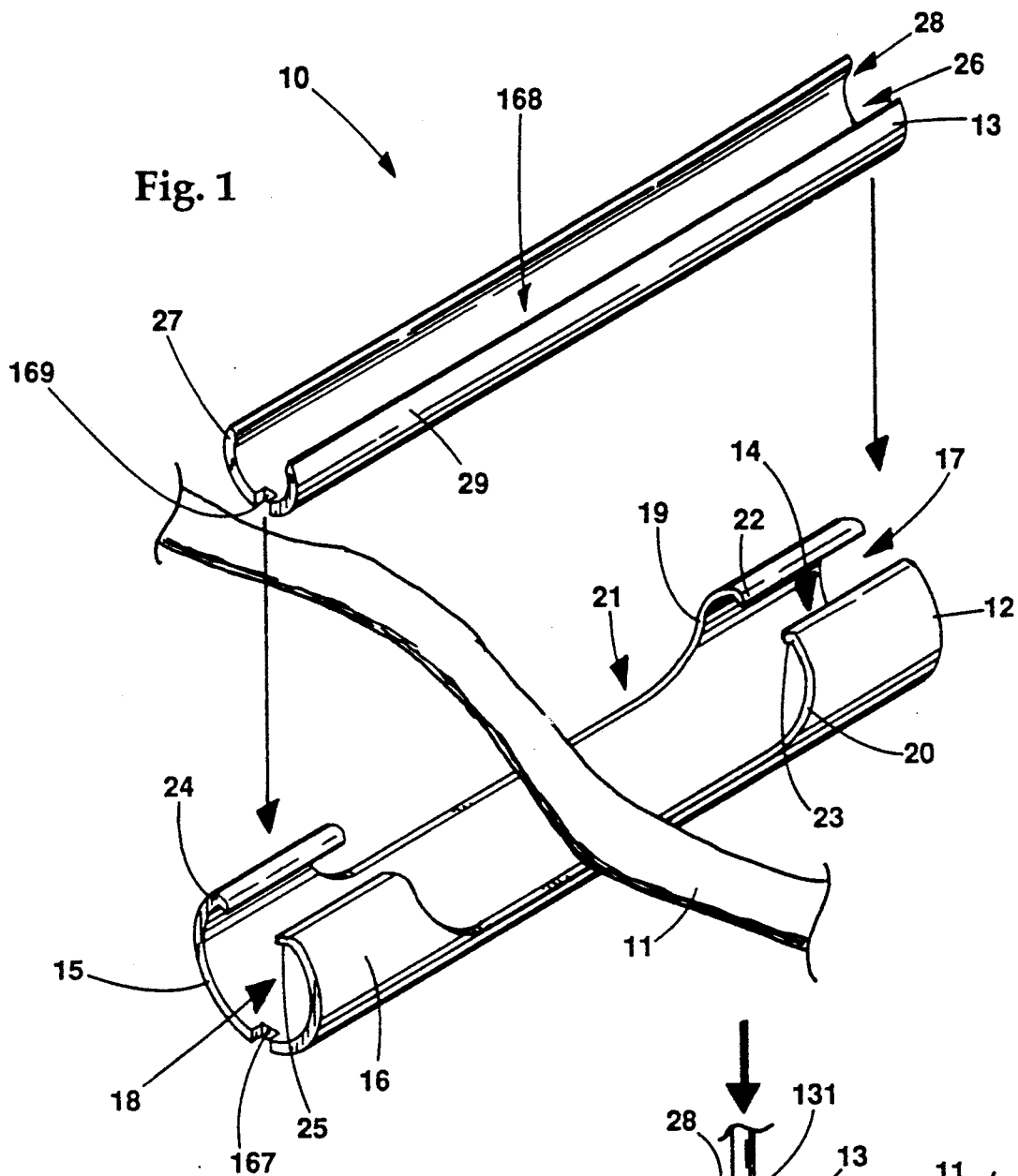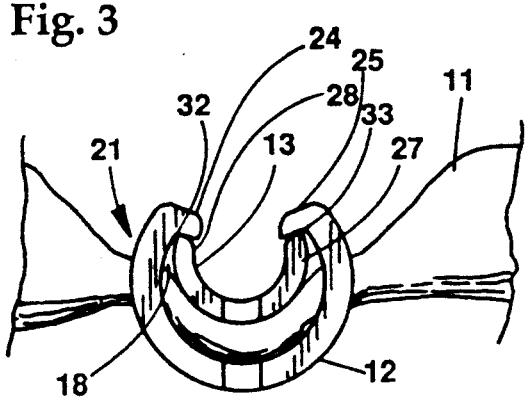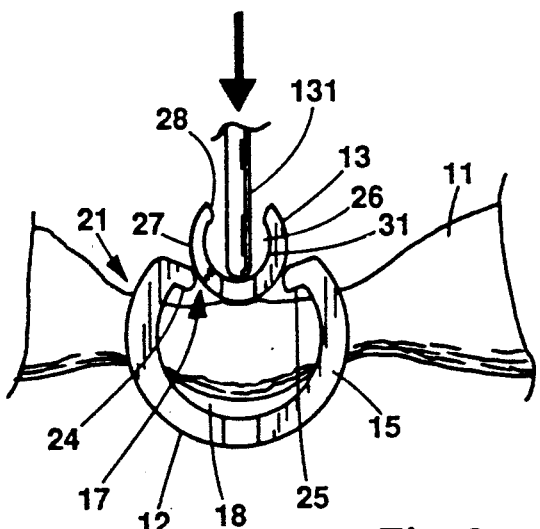

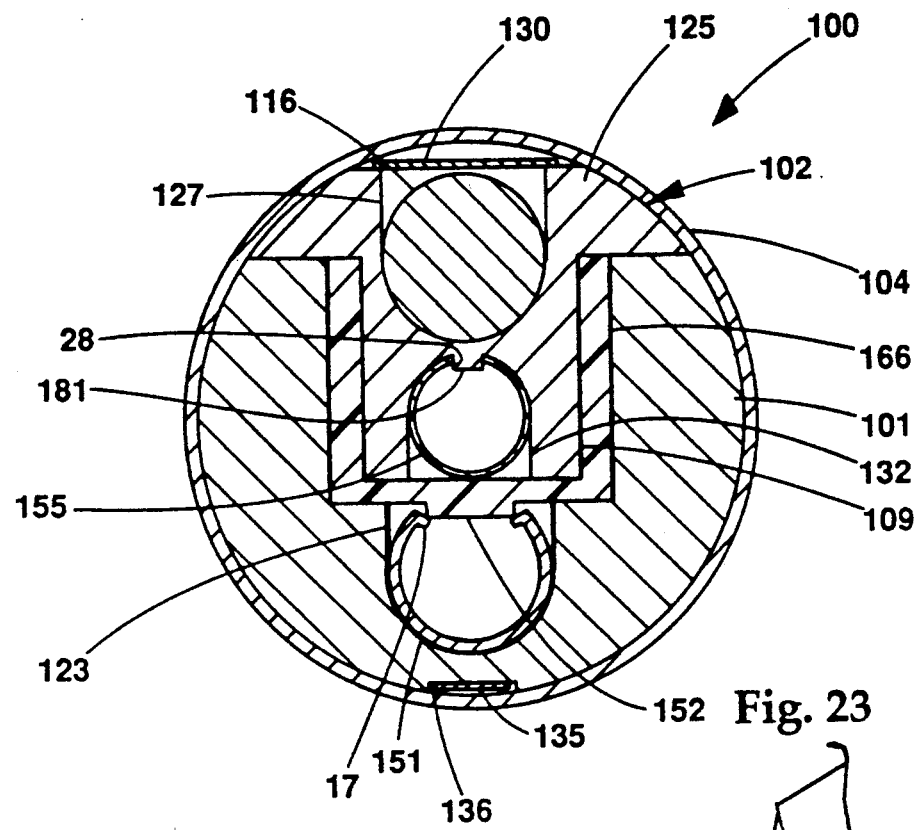
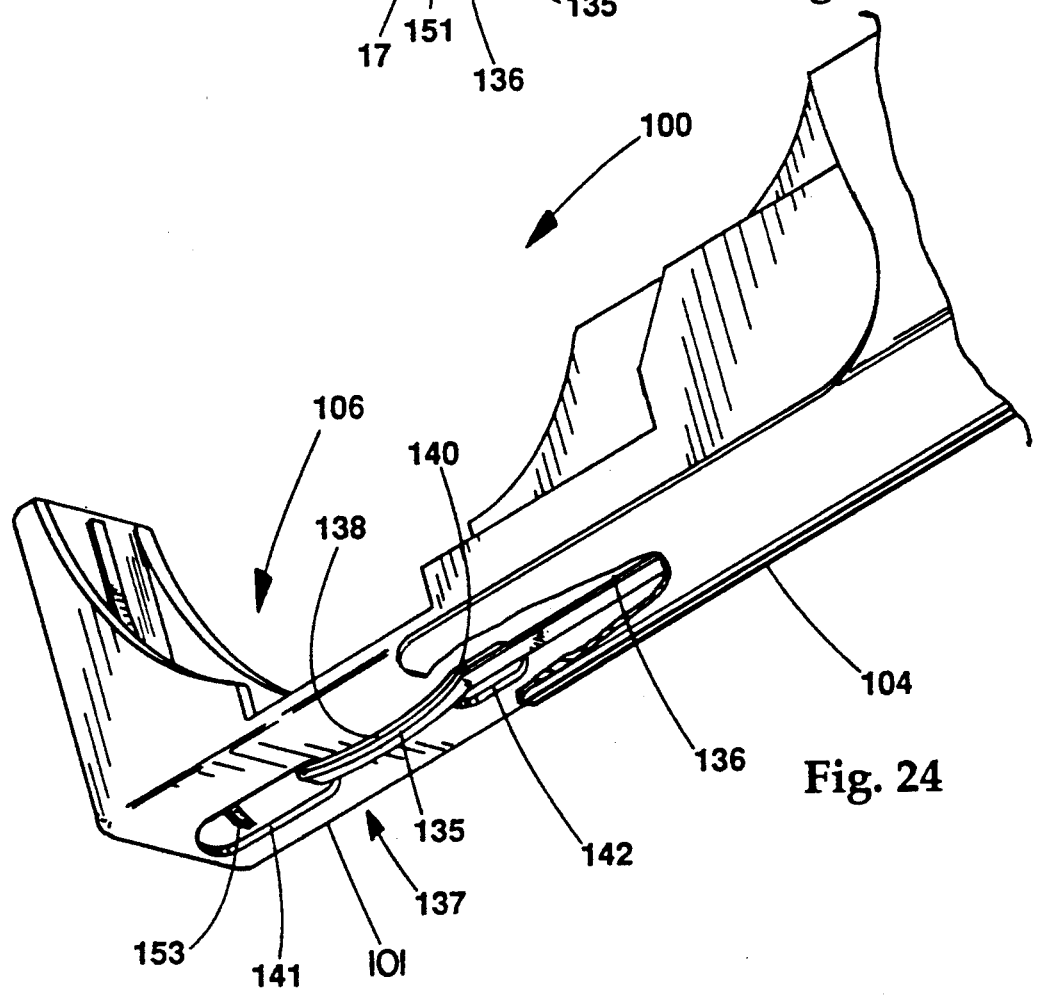

TWO PART SURGICAL LIGATING CLIP, APPLICATOR AND METHOD OF USE

TECHNICAL FIELD

This invention relates generally to surgical clips for ligating vessels and ducts and particularly to a surgical ligating clip having at least two separate pieces, an applicator therefor and a method of using the clip and the applicator.

BACKGROUND OF THE INVENTION

Several different types of one-piece surgical clips are known for ligating vessels and ducts. One type utilizes a V-shape for pinching the vessel closed between the straight legs of the one-piece clip. A problem with this V-shaped configuration is that as the legs of the clip are brought together, the vessel is commonly pushed either partially or completely out from between the free ends of the legs. In addition, vessels and ducts of the human body are inherently slippery and very elastic, which compounds the problem of open-ended clips being unable to completely ligate or clamp a vessel shut. To combat these problems, physicians typically strip or dissect tissue from a vessel to be ligated for circumferential exposure. Even then, the physician must push the open-ended clip against the vessel and away from his line of sight. Knowing this, physicians typically place additional ligating clips in an effort to ensure that a vessel or duct is completely clamped shut. A problem with this approach is that many needless clips are utilized and that the length of an exposed vessel or duct can be limited for the placement of these additional clips. Another problem is that loose or detached clips must be retrieved, which is time consuming, particularly in an endoscopic procedure. One solution to this problem has been to utilize a modified V-shaped configuration in which a knee-bend is formed in each of the legs. This modified V-shaped configuration allows the bent legs to be closed in a parallel manner. However, vessels still slip or slide out of these modified V-shaped ligating clips during application to a vessel or duct.

Another type of one-piece surgical clip employs a generally U-shaped configuration and also closes in a parallel manner similar to the modified V-shaped clip. However, the position of the kink formed in the U-shaped bend during closure of the clip must be carefully controlled to maintain the relative position of the legs. Otherwise, the U-shaped clip becomes V-shaped with all the aforementioned problems of vessel slippage.

Although the U-shaped clip and the knee bend in each of the legs of the modified V-shaped clip are intended to reduce vessel slippage out the open end, vessels are still very wet and slippery and tend to slide out of these open-ended clips. To further reduce vessel slippage out of the U-shaped and modified V-shaped clips, serrations or indentations have been formed on the inside of the legs for gripping and holding the vessel during closure of the clip. In spite of these multiple improvements to reduce slippage of the vessel out the open end, the vessel is often not completely clamped shut by the clip, thus requiring placement of additional ligating clips.

Another modification to the U-shaped or modified V-shaped one-piece clip is the use of a hook and catch at the ends of the legs. This hook and catch combination provides closure around the entire circumference of the vessel, thus reducing the problem of vessel slippage out the open end of the clip. However, this hook and catch combination often does not close around oversized vessels and is susceptible to reopening due to lateral or up-and-down movement of the clip legs. When the hook and catch disengages, the vessel can slide, once again, out the open end of the clip. In an attempt to correct this disengagement problem, several one-piece hook and catch clips include one or more lateral stops. The lateral stops reduce lateral or up-and-down movement of the hook and catch in opposite directions.

A separate two-piece clip is used to bridge an incision in fascia tissue, but not to ligate a vessel or duct. The fascia clip includes an elongated base and a flexible strap that is passed through separate openings at the opposite ends of the base. The base is sized to bridge over the incision. The strap has a pointed distal end for passage through the opening at one end of the base, through the fascia tissue, and under the incision. An applicator holding the fascia tissue in position directs the distal end of the strap once again through the fascia tissue on the other side of the incision and through the opening at the opposite end of the clip base. An enlarged head at one end of the strap prevents passage through one opening of the strap, while teeth at the other end of the strap engage the opening at the opposite end of the strap. Although suited for bridging an incision in fascia tissue, this two-piece fascia clip is not suitable for duct or vessel ligation due to the construction of the required clip applicator. In addition, this two-piece fascia clip is unsuitable for minimally invasive procedures, which typically utilize a hollow 10 mm access sheath.

SUMMARY OF THE INVENTION

The foregoing problems are solved and a technical advance is achieved in an illustrative two-piece surgical ligating clip that circumferentially surrounds a vessel and securably positions the vessel between the two pieces of the clip. The clip is preferably suited for ligating vessels, ducts, and the like through a trocar access sheath during a minimally invasive surgical procedure. However, the ligating clip can be used equally as well in any open surgical procedure. In addition, this two-piece clip advantageously allows the physician to see circumferential ligation of a vessel or duct as well as to know that the clip will not slip or slide off the vessel or duct. This illustrative surgical ligating clip comprises a first piece having an outer surface and a preformed channel including an opening in the outer surface for advantageously positioning a vessel to be ligated therein. The clip further comprises a second piece separate from the first piece which is securably positionable in the channel of the first piece to securably and circumferentially position the vessel between the first and second pieces of the clip without slippage therefrom.

To advantageously increase the number of fastening possibilities, the first piece further includes a second channel. The second piece is securably positionable in at least one of the first and second channels. In this aspect, the vessel is positioned again, for example, in the first channel of the first piece, and the second piece assumes any number of different shapes and configurations for placement in at least one of the first and second channels for securably positioning the vessel in the first channel between the first and second pieces.

In another aspect of the surgical ligating clip, the second channel includes a second opening in the outer surface of the first piece. The second piece is securably positionable in at least one of the first and second channels through at least one of the first and second openings for extending into the other of the first and second channels. In this aspect, the second piece is advantageously inserted through an opening in the outer wall of the first piece other than or in addition to the opening through which the vessel is positioned. Additionally, the second opening communicates with the first opening for transversely positioning the ligating clip with respect to the vessel or duct. The second piece is advantageously positioned in the first passage of the first piece through either one or both of the openings.

In the preferred embodiment, the first piece of the clip comprises a cylindrical, elastic material tube having a first preformed channel including a passage extending longitudinally therein and a longitudinal slot formed in an outer wall of the tube, which communicates with the passage of the tube. The width of the longitudinal slot is less than the width of the passage for advantageously securably positioning the second piece in the passage of the first tube and circumferentially ligating the vessel positioned between the two pieces. The first piece tube also has a second channel including first and second openings communicating with and on opposite sides of the longitudinal slot. Each of the openings has a predetermined height and width which form the ends of the second channel for insertion of a vessel through the outer wall. The outer wall further includes projections extending therefrom adjacent the slot and into the passage of the first tube. The clip also includes a second, elastic material tube separate from the first tube. Similarly, the second tube has a second passage extending longitudinally therein, a width greater than the width of the slot of the first tube and less than the width of the passage of the first tube, and an outer wall having a longitudinal slot therein for compression of the second tube and passage of the second tube through the slot and into the passage of the first tube. Advantageously, the outer wall adjacent the longitudinal slot of the second tube engages the projections of the first tube when the second tube is passed through the slot and positioned in the passage of the first tube for securely positioning between the two tubes a vessel positioned in the second channel of the first tube.

The present invention also includes an applicator for advantageously applying the surgical ligating clip circumferentially and securably about a vessel, duct, or the like. As previously described, the clip includes a first piece having an outer surface and a preformed channel including an opening in the outer surface. The clip also includes a second piece separate from the first piece and positionable in the channel, whereby a vessel is ligated between the first and second pieces when the vessel is positioned in the channel and the second piece is securably positioned in the channel. The applicator comprises a housing and an insertion mechanism. The housing has a distal end and a vessel channel positioned thereabout with a vessel access opening communicating with the opening of the first piece when positioned in the vessel channel. The insertion mechanism has a distal end, a delivery position, and a delivery passage positioned about the distal end of the insertion mechanism. The delivery passage communicates with the channel of the first piece when the insertion mechanism is positioned in the delivery position. The insertion mechanism also includes an insertion projection responsive to a force moving the insertion projection into the delivery passage and engagement with the second piece for positioning the second piece from the delivery passage into the channel of the first piece and circumferentially and securably ligating the vessel between the two pieces.

When the first piece of the surgical ligating clip further includes a second channel, the second piece is positionable in at least one of the first and second channels. The delivery passage of the insertion mechanism of the applicator then communicates with the first opening of the first piece when the insertion mechanism is positioned in the delivery position. The insertion projection of the mechanism is then responsive to the force moving the insertion projection into the delivery passage for positioning the second piece into at least one of the first and second channels of the first clip piece.

When the second channel includes an opening in the outer surface of the first piece, the vessel access opening positioned about the distal end of the applicator housing advantageously communicates with at least one of the first and second openings of the first piece when positioned in the vessel channel. The insertion mechanism of the applicator communicates with at least one of the first and second channels of the first piece when the insertion mechanism is positioned in the delivery position. The insertion projection of the mechanism is responsive to the force moving the insertion projection into the delivery passage and engagement with the second piece for positioning the second piece from the delivery passage into at least one of the first and second channels of the first clip piece through at least one of the first and second openings of the first clip piece.

The applicator further comprises a trigger connected to the insertion mechanism for positioning the insertion mechanism in the delivery position, moving the projection into said delivery passage and engagement with the second piece and positioning the second piece from the delivery passage into at least one of the first and second channels of the first clip piece through at least one of the first and second openings of the first clip piece. The insertion mechanism also includes a carriage positioned within the guide channel of the housing and an insertion projection channel wherein the insertion projection is positioned. The insertion projection further includes a push rod positioned in the insertion projection channel and a clamping arm pivotedly connected to the push rod for movement through the delivery passage. The carriage also includes a deflection arm positioned about the delivery passage for guiding the clamping arm into the delivery passage when the push rod is urged toward the distal end of the carriage. A handle connected to the housing includes a grip with the trigger pivotedly connected to the grip and the insertion projection.

The applicator further comprises a clip ejector positioned in an ejector channel of the housing for advantageously ejecting the clip and ligated vessel from the applicator. The clip ejector has a relaxed position, an ejected position, and a distal end extending into the vessel channel when in the ejected position for ejecting the ligated vessel and clip from the vessel channel. The proximal end of the clip ejector is releasably connected to the trigger when in the ejected position. A release mechanism is advantageously provided in the handle for releasing the clip ejector from the trigger when the clip ejector is in the ejected position.

With respect to the preferred embodiment of the surgical ligating clip in which the first and second pieces include tubes, the first tube includes first and second openings communicating with and on opposite sides of the longitudinal slot for insertion of a vessel through the outer wall. The applicator for this preferred embodiment of the clip comprises a housing in which the vessel channel communicates with the first and second openings of the first tube when positioned in the vessel channel. The delivery passage of the insertion mechanism communicates with the first passage of the first tube when the insertion mechanism is positioned in the delivery position about the distal end of the housing. The insertion projection is responsive to a force moving the insertion projection into the delivery passage when the insertion mechanism is in the delivery position and positioning the second tube, when in the delivery passage, from the delivery passage into the first passage of the first tube through the slot thereof for advantageously ligating between the first and second tubes a vessel or duct positioned through the first and second openings of the first tube.

The housing of the applicator for the preferred embodiment of the clip includes a guide channel extending longitudinally therein. The insertion mechanism of the applicator includes a carriage slidably positioned within the guide channel of the housing. The applicator further comprises a trigger connected to the carriage and the insertion projection. The trigger is responsive to a force, such as from the attending physician, that positions the carriage in the delivery position, moves the insertion projection into the delivery passage and engagement with the second tube when the carriage is in the delivery position, and positions the second tube from the delivery passage into the first passage of the first tube through the longitudinal slot thereof.

The insertion projection of the applicator for the preferred embodiment includes a push rod positioned in an insertion projection channel of the carriage and a clamping arm pivotedly connected to the push rod for moving the clamping arm through the delivery passage. The carriage further includes a deflection arm positioned about the delivery passage for guiding the clamping arm into the delivery passage of the carriage when the push rod is urged toward the distal end of the carriage. The applicator further comprises a handle that is connected to the housing and includes a grip. The trigger is pivotedly connected to the grip, and a spring is connected to the grip and the trigger for urging the trigger into a released position. Another spring is positioned between the trigger and carriage for relaxing the connection between the trigger and carriage when in the delivery position.

A clip ejector positioned in an ejector channel of the housing has a relaxed position, an ejected position, and a distal end extending into the vessel channel when in the ejected position. The proximal end of the clip ejector is releasably connected to the trigger when the clip ejector is in the ejected position. Yet another spring is connected to the proximal end of the clip ejector for urging the clip ejector to the relaxed position. The handle further includes a release mechanism for engaging the proximal end of the clip ejector and releasing the clip ejector from the trigger when the clip ejector is in the ejected position.

The housing of the applicator for the preferred embodiment of the clip further includes a stop positioned at the distal end thereof for engaging the distal end of the carriage when in the delivery position. The housing further includes a first tube passage communicating with the vessel channel and still another spring communicating with a plurality of first tubes when positioned therein for urging the plurality toward the distal end of the housing. A positioning projection extends into the first tube passage of the housing and into the longitudinal slot of each of the first tubes for advantageously orienting the first tube in the vessel channel for receipt of the second tube. Another position projection extends from the stop of the housing and into the slot of a first tube in the vessel channel for maintaining the orientation of the first tube in the vessel channel for receiving a vessel in the first and second openings thereof. The carriage includes a second tube passage communicating with the delivery passage and yet still another spring communicating with this plurality of tubes when positioned therein for urging the plurality of second tubes toward the delivery passage. The applicator further comprises an outer sleeve having a passage extending longitudinally therein for containing the housing, carriage and insertion mechanism for advantageous insertion through a minimally invasive access sheath. The handle of the applicator is connected to the proximal end of the outer sleeve.

The method of ligating a vessel utilizing one configuration of the clip of the present invention includes positioning a vessel in the channel through the opening in the outer surface of the first piece and securably positioning the second piece in the channel of the first piece. The step of positioning the vessel includes positioning a first piece in the vessel channel of an aforementioned applicator and positioning the vessel in the channel of the first piece and the vessel channel of the applicator. The step of securably positioning the second piece includes positioning the second piece in the delivery passage of the applicator and applying force to the trigger of the applicator that moves the insertion projection into the delivery passage and positions the second piece from the delivery passage into the channel of the first clip piece.

In the method of ligating a vessel utilizing another configuration of the clip of the present invention, the vessel is positioned in the first channel of the first piece through the first opening in the outer surface of the first piece. The method further includes securably positioning the second piece in at least one of the first and second channels. The step of positioning the vessel in at least one of the channels includes positioning the first piece in the vessel channel of an aforementioned applicator and positioning the vessel in the first channel of the first piece through the vessel access opening of the housing of the aforementioned applicator. The step of securably positioning the second piece in at least one of the channels includes positioning the second piece in the delivery passage of the applicator and applying force to the insertion projection of the applicator. This force moves the insertion projection into the delivery passage and positions the second piece from the delivery passage into at least one of the channels of the first piece.

In the method of ligating a vessel utilizing still another configuration of the clip of the present invention, the vessel is positioned in at least one of the channels through at least one the openings of the first piece. The second piece is securably positioned in at least one of the channels through at least one of the openings of the first piece. The step of positioning the vessel in at least one channel includes positioning the first piece in the vessel channel of an aforementioned applicator and positioning the vessel in at least one of the channels of the first piece through the vessel access opening of the housing of the aforementioned applicator. The step of securably positioning the second piece includes positioning the second piece in the delivery passage of the applicator and applying force to the insertion projection of the applicator. This force moves the insertion projection into the delivery passage and positions the second piece from the delivery passage into at least one of the channels of the first piece through at least one of the openings of the first piece.

BRIEF DESCRIPTION OF THE DRAWINGS

FIG. 1 depicts a pictorial view of an illustrative two-piece surgical ligating clip of the present invention;

FIG. 2 depicts an end view of the two-piece ligating clip of FIG. 1 with the second piece being inserted into the passage of the first piece tube;

FIG. 3 depicts an end view of the clip of FIG. 1 with the second piece tube securably positioned in the passage of the first piece tube and circumferentially ligating a vessel positioned therebetween;

FIG. 23 depicts an enlarged, cross-sectional view of the applicator of FIG. 15 taken along the line 23—23;

FIG. 24 depicts an enlarged, partially-sectioned pictorial view of the underside of the distal end of the applicator of FIG. 15.

DETAILED DESCRIPTION

Figure 4:
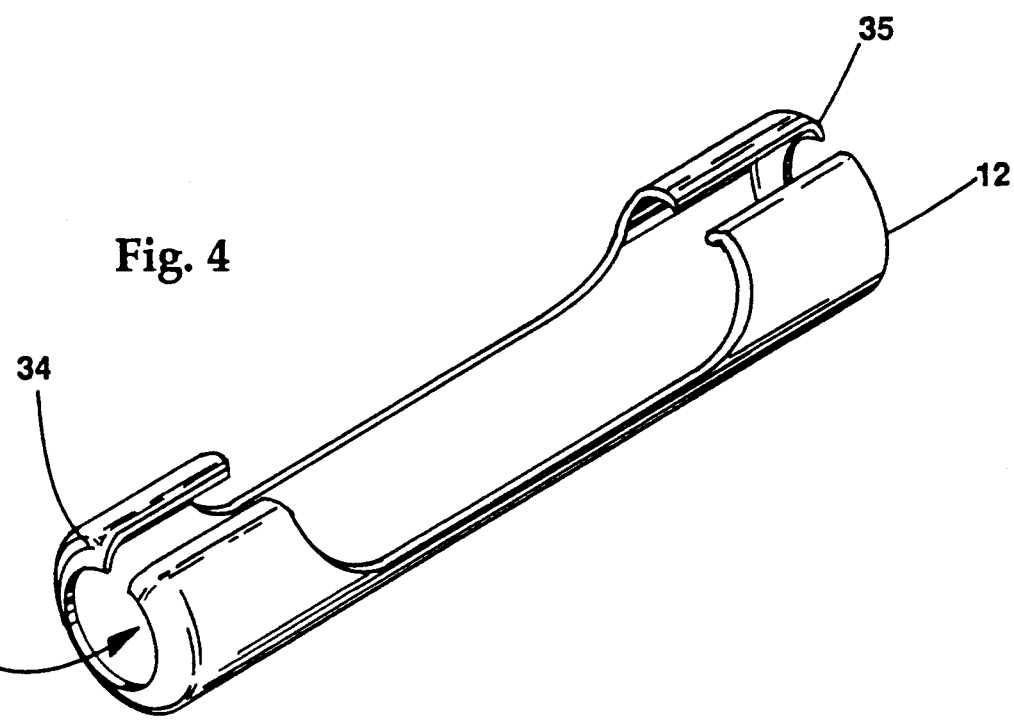
FIG. 4 depicts a pictorial view of the first piece of the surgical ligating clip of FIG. 1 with the ends thereof annularly closing.

Depicted in FIG. 1 is a pictorial view of an illustrative two-piece surgical ligating clip 10, which represents the preferred embodiment of the present invention. Surgical clip 10 is for circumferentially ligating vessel 11, a duct, or the like. The surgical clip comprises a first piece 12 and a second piece 13 separate from the first piece and securably positionable in first preformed channel 14 of the first piece for ligating vessel 11 positioned therebetween. The first piece 12 comprises an at least partially cylindrical, elastic material tube having a hollow passage 18 extending longitudinally therein. Elastic material tube 12 preferably comprises, for example, Series 300 stainless steel and has a maximum outside diameter of approximately 0.088" with outer wall 15 approximately 0.012" thick. The elastic material tube can also comprise titanium or any other biocompatible or biodegradable elastic material. Tube 12 is approximately 0.433" long and 0.074" high. Preformed channel 14 includes passage 18 and longitudinal slot 17 passing through outer wall 15 and outer surface 16 and communicating with passage 18. The width of passage 18 is approximately the inside diameter of the tube. The minimum width of longitudinal slot 17 is approximately 0.040", which is less than the width of passage 18 or the inside diameter of the tube. Second piece tube 13 is securably positioned in preformed channel 14 through longitudinal slot 17 and into passage 18 for ligating vessel 11 between tubes 12 and 13. First piece tube 12 also includes second preformed channel 21, which is transverse to and communicates with first preformed channel 14. Second channel 21 has first and second, opposite end openings 19 and 20. Openings 19 and 20 in outer surface 16 are on opposite sides of longitudinal slot 17 and pass through outer wall 15. Each of openings 19 and 20 is centered along the length of the tube and has a width of approximately 0.276" and a height of approximately 0.045" for insertion of vessel 11 through outer wall 15 of the tube and into second channel 21. The outer wall includes tangs or projections 22-25 extending therefrom adjacent first longitudinal slot 17 and into passage 18. Each of these tangs or projections are approximately 0.079" long and 0.007" wide. Notch 167, approximately 0.007" deep and 0.012" wide, is cut into the bottom of passage 18 at each end of the tube. These notches are used to position the tube in a hereinafter described applicator.

Second piece 13 comprises an at least partially cylindrical, elastic material tube separate from the first tube and having a third preformed channel 168 extending longitudinally therethrough. The elastic material preferably comprises Series 300 stainless steel. However, the elastic material can also comprise titanium or any other biocompatible or biodegradable elastic material. First and second tubes 12 and 13 can be of the same elastic material or dissimilar elastic materials. Second tube 13 has a maximum outside diameter of approximately 0.052" with outer wall 27 approximately 0.010" thick. The maximum width of the second tube is greater than the width of first slot 17 and less than the width of first passage 18 of the first tube. The second tube is approximately 0.433" long and 0.032" high. Third channel 168 includes hollow passage 26 and longitudinal slot 28, which passes through outer wall 27 and outer surface 29 of the tube and communicates with second passage 26. Notch 169, approximately 0.007" deep and 0.012" wide, is cut into the bottom of passage 26 at each end of the tube. Second longitudinal slot 28 is for compression of the second tube and passage of the tube through first slot 17 and into first passage 18 of the first tube. Second longitudinal slot 28 is approximately 0.035" wide for compression of second tube 13 through longitudinal slot 17 of first tube 12. Similarly, longitudinal slot 17 of the first tube is expandable for passage of the second tube therethrough. When fully inserted through first longitudinal slot 17 and into passage 18 of the first tube, the edges of outer wall 27 adjacent second longitudinal slot 28 engage tangs or projections 22-25 extending into passage 1ʳ of the first tube for securely positioning and locking the second tube in the passage of the first tube and circumferentially ligating vessel 11 positioned in channel 21 between the two tubes.

Depicted in FIG. 2 is an end view of tubes 12 and 13 with vessel 11 positioned in second channel 21 of the first tube. A clamping finger 131 of an applicator (not shown) extends through second longitudinal slot 28 and into passage 26 of second tube 13. Clamping finger 131 engages inside surface 31 of outer wall 27 to engage outer wall 15 and projections 22-25 of the first tube. As clamping finger 131 continues to apply force to the first and second tubes, second tube 13 compresses and longitudinal slot 17 of first tube 12 expands to pass the second tube through the slot and into passage 18 of the first tube.

Depicted in FIG. 3 is an end view of first and second tubes 12 and 13 with the second tube securably positioned in passage 18 of the first tube. When securably positioned in the passage of the first tube, edges 32 and 33 of outer wall 27 of the second tube about longitudinal slot 28 engage tangs or projections 22—25 of the first tube to securably position and lock the second tube in passage 18 of the first tube. As a result, vessel 11 positioned in second channel 21 of the first tube is circumferentially ligated between first and second tubes 12 and 13.

Depicted in FIG. 4 is a pictorial view of first tube 12 with opposite ends 34 and 35 of the tube rounded to annularly close on passage 18 of the tube. The annularly closing opposite ends of the tube prevent the second tube from longitudinally sliding out of passage 18 of the first tube.

Figure 5:
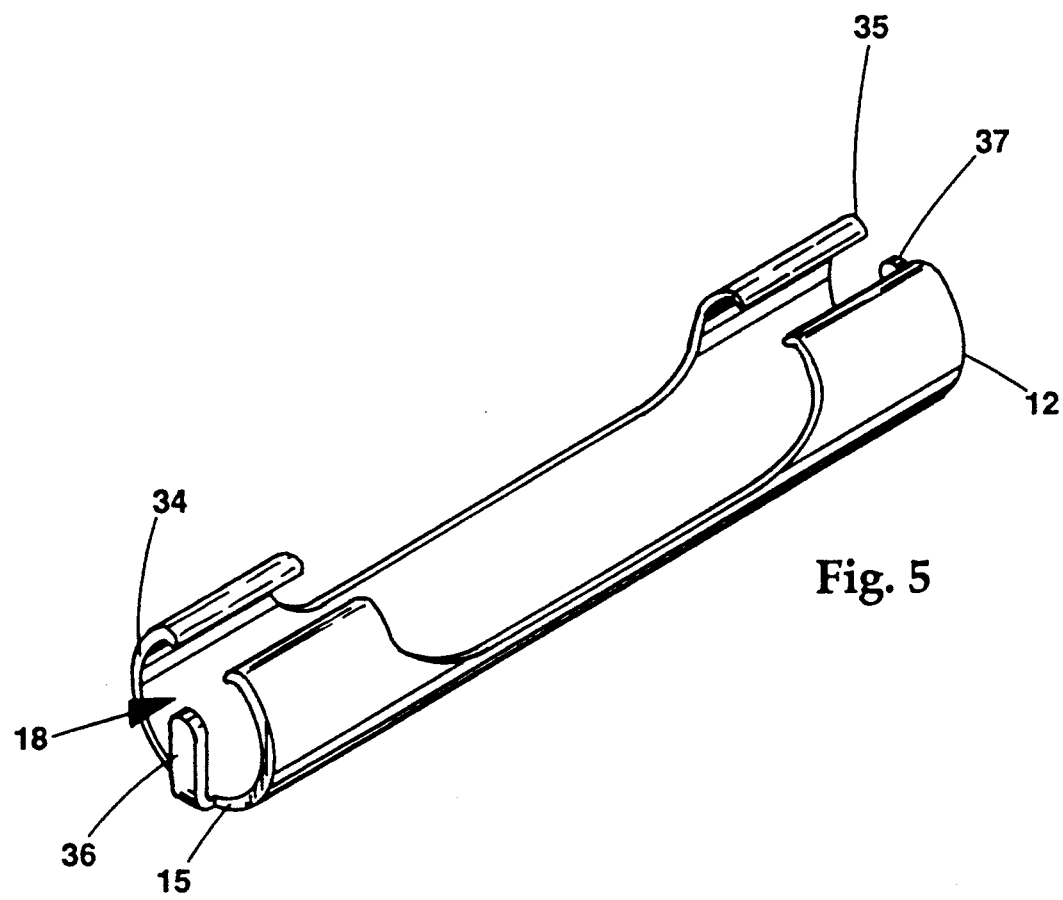
FIG. 5 depicts a pictorial view of the first piece of the surgical ligating clip of FIG. 1 with the opposite ends having projections extending from the outer wall and into the passage of the first piece tube.

Depicted in FIG. 5 is a pictorial view of first tube 12 with opposite ends 34 and 35 having respective projections 36 and 37 extending from outer wall 15 an into passage 18 for preventing the second tube from sliding out the ends of the passage.

Figure 6:
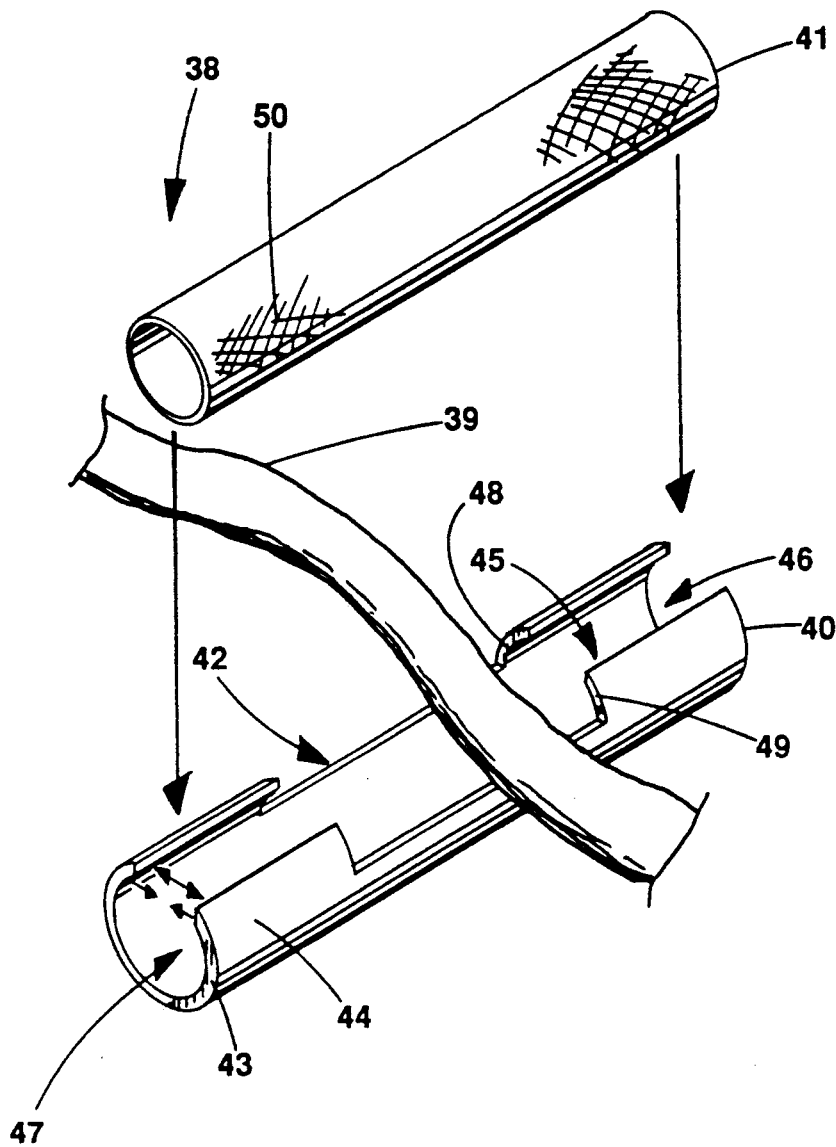
FIG. 6 depicts another aspect of the surgical ligating clip of the present invention.

Depicted in FIG. 6 is a pictorial view of two-piece surgical ligating clip 38, which illustrates another aspect of the present invention, for circumferentially ligating vessel 39 positioned between first and second pieces 40 and 41 and in second preformed channel 42 of the first piece. First piece 40 comprises an elongated member, cylindrical tube having a partially circular cross-sectional shape, outer wall 43 and outer surface 44. The first piece tube also includes first preformed channel 45 including first passage 47 and first longitudinal slot opening 46 in outer wall 43 and outer surface 44 communicating with the first passage. Second channel 42 includes openings 48 and 49 on opposite sides of and communicating with first longitudinal slot opening 46. Second channel 42 is for positioning vessel 39 therein and is transverse to and communicates with first channel 45 of the first piece tube. First elongated member tube 40 has passage 47 extending longitudinally therethrough and longitudinal slot opening 46 passing through the outer wall and surface and communicating with the passage. First channel 45 includes longitudinal slot opening 46 and passage 47 for inserting second piece 41 through the longitudinal slot opening and into the passage of the first tube. As similarly described with respect to the first tube of FIG. 1, passage 47 has a first width, and first longitudinal slot opening 46 has a second width less than the width of passage 47. Openings 48 and 49 in outer wall 43 of first tube 40 are on opposite sides of slot opening 46 and form the opposite ends of second channel 42 for positioning vessel 39 therein. Each of openings 48 and 49 have a predetermined height and width in the outer wall of the tube for positioning vessel 39 in second channel 42.

Second piece 41 comprises a second elongated member of, for example, either a cylindrical tube or rod, which has a maximum width less than the width of first passage 47 of the first tube and greater than the width of slot opening 46 of the first tube. Second piece 41 has well-known textured surface 50 for engaging the edges of slot opening 46 of the first piece tube. The first tube comprises a well-known elastic material which permits slot opening 46 to expand for the passage of the second tube therethrough and into passage 47 of the first tube.

Figure 7:
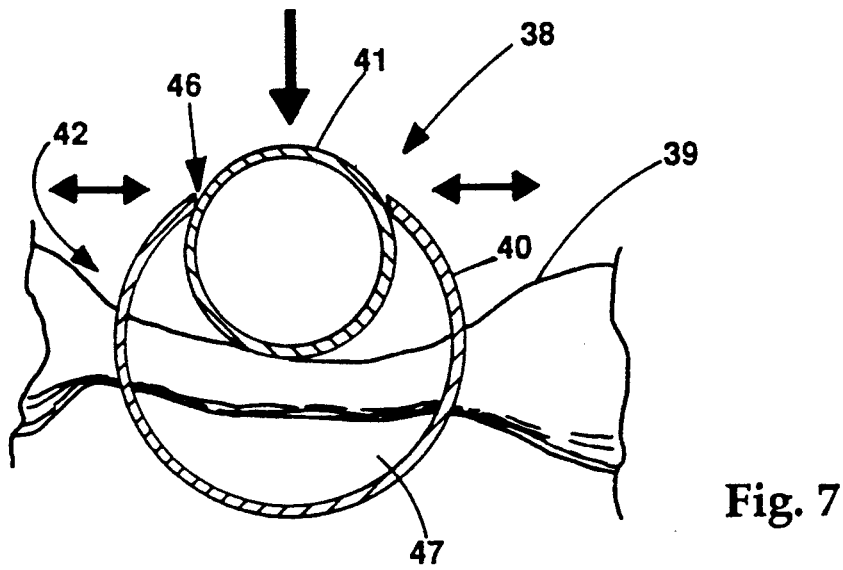
FIG. 7 depicts an end view of the surgical ligating clip of FIG. 6 ligating a vessel positioned between the two pieces.

Depicted in FIG. 7 is an end view of surgical clip 38 of FIG. 6 in which second tube 41 is securably positioned in passage 47 of first tube 40, thereby circumferentially between the two tubes vessel 39 positioned in second channel 42 of the first tube. To securably lock the vessel in the second channel of the first tube, the center of second tube 41 must be positioned within passage 47 of the first tube and within or below longitudinal slot opening 46.

Figure 8:
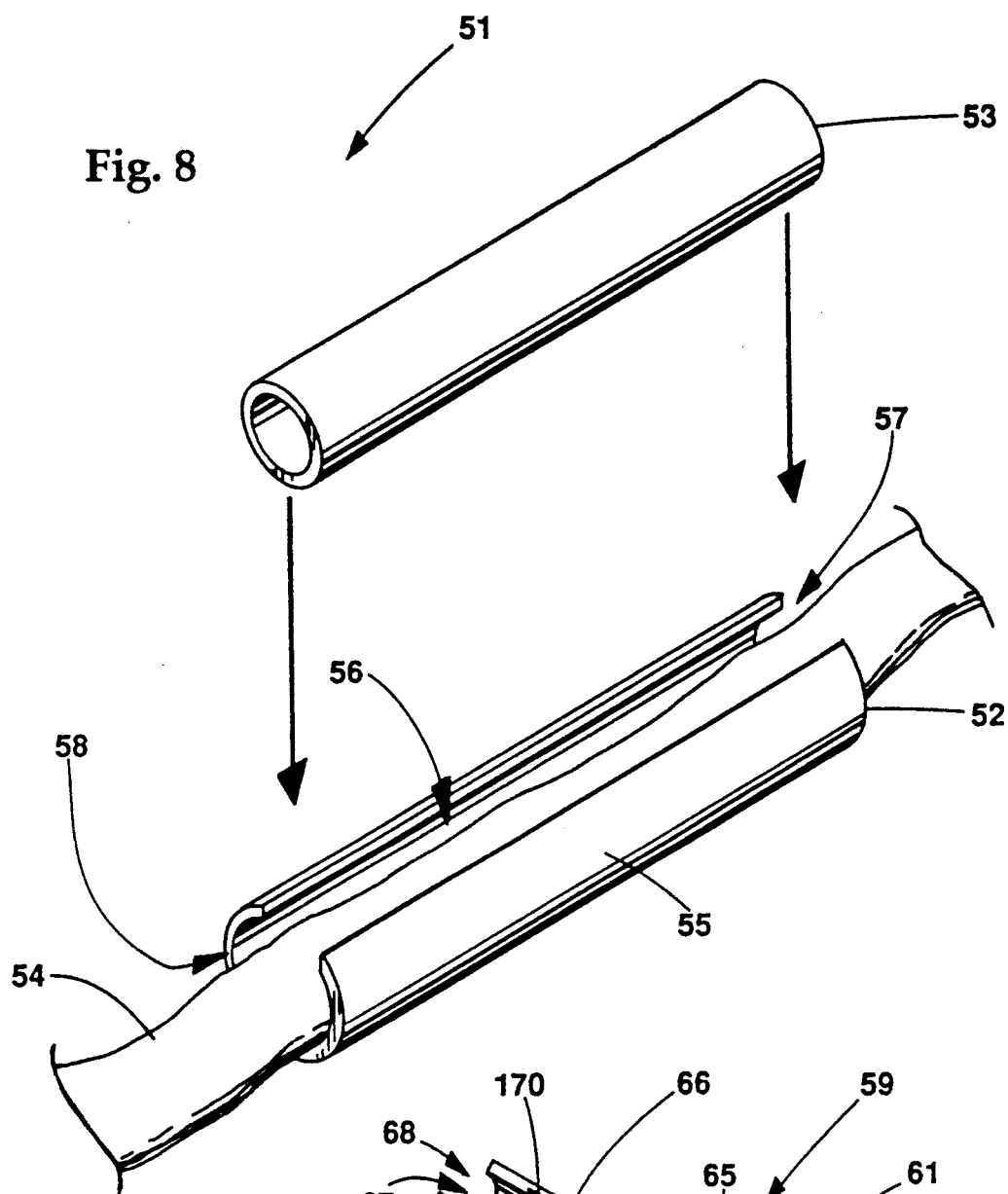
FIG. 8 depicts still another aspect of the surgical ligating clip of the present invention.

Depicted in FIG. 8 is a pictorial view of surgical ligating clip 51, which illustrates still another aspect of the present invention, comprising first and second pieces 52 and 53 for ligating vessel 54. First piece 52 comprises an elongated member tube having an outer surface 55 and preformed channel 56 including a longitudinal slot opening 57 formed in the outer surface thereof. Channel 56 also includes passage 58 that has a maximum width wider than longitudinal slot opening 57. Vessel 54 is positioned through longitudinal slot opening 57 and into passage 58 of channel 56 in the first elongated member tube. Second piece 53 is separate from the first piece and is securably positionable in passage 58 of channel 56 through longitudinal slot opening 57. Second piece 53 is also an elongated member tube or rod. The width of second piece 53 is greater than that of longitudinal slot opening 57, but less than that of passage 58. When the vessel is positioned in channel 56 of the first tube, second piece 53 is passed through expandable longitudinal slot opening 57 and into passage 58 to circumferentially ligate the vessel.

Figure 9:
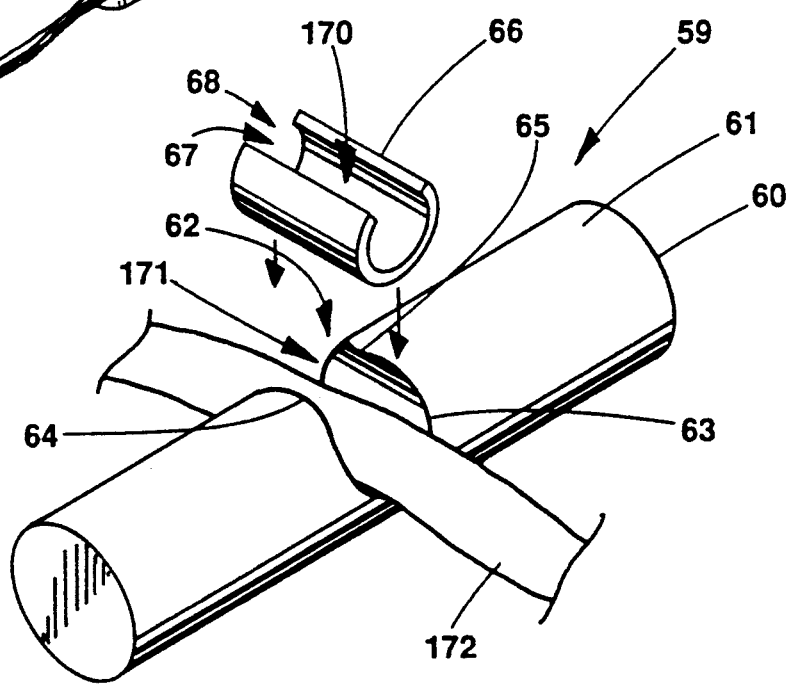
FIG. 9 depicts yet another aspect of the two-piece surgical ligating clip of the present invention and is a variation of the clip of FIG. 8.

Depicted in FIG. 9 is a pictorial view of two-piece surgical ligating clip 59, which illustrates yet another aspect of the present invention, and is a variation of surgical clip 51 of FIG. 8. Clip 59 comprises first elongated member piece 60 having outer surface 61 and preformed channel 62 including passage 171 and opening 63 in the outer surface thereof. First elongated member piece 60 comprises a cylindrical rod with channel 62 formed therein by drilling a hole transversely through the rod and cutting through outer surface 61 of the rod to form projections 64 and 65 about the middle portion of channel 62 as shown. Second elongated member piece 66, separate from first piece 60, comprises an at least partially cylindrical tube with channel 170 extending longitudinally therein. Channel 170 includes passage 67 and a longitudinal slot opening 68 formed through the outer surface thereof and communicating with passage 67. As a result, second elongated member piece 66 can be compressed for insertion into passage 171 of the first piece. The width of the second elongated member piece 66 is less than the width of passage 171 but greater than opening 63 between projections 64 and 65. Vessel 172 is positioned in first channel 62 of first piece 60 in which second piece 66 is compressed between projections 64 and 65 and into passage 171 for circumferentially ligating the vessel.

Figure 10A:
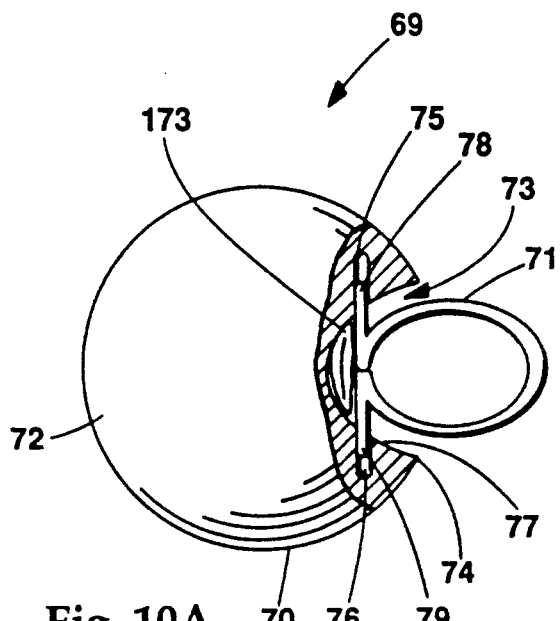
FIGS. 10A and 10B depict still yet another aspect of the two-piece surgical clip of the present invention.
Figure 10B:
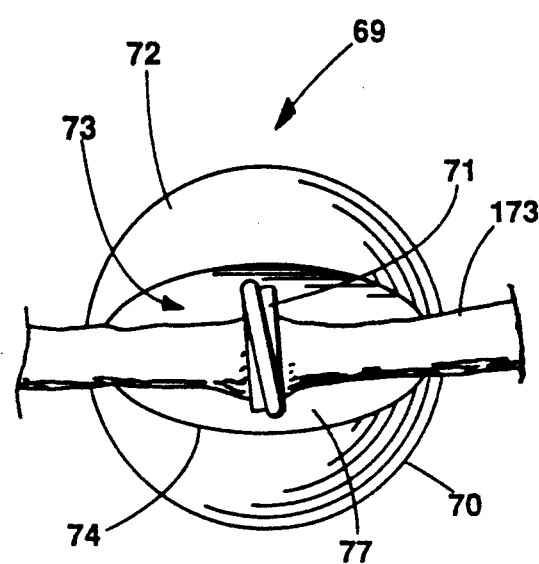

Depicted in FIGS. 10A and 10B are a partially sectioned side view and a top view of two-piece surgical clip 69 including first spherical piece 70 and second spring piece 71, which represents still yet another aspect of the present invention. First spherical piece 70 includes an outer spherical surface 72 and first preformed channel 73 including a first opening 74 in the outer surface. A second preformed channel including oppositely facing indentations 75 and 76 is formed in inner surface 77 of first channel 73. The second channel, including indentations 75 and 76, communicates with first channel 73. Second spring piece 71 is separate from the first piece and comprises an omega-shaped piece of elastic material wire having opposite ends 78 and 79 for insertion into indentations 75 and 76 in the surface of first channel 73. Vessel 173 is positioned in channel 73 of the first spherical piece and compressed. Second spring piece 71 is compressed to bring opposite ends 78 and 79 closer together for insertion into first channel 73. Opposite ends 78 and 79 of the second spring piece are aligned with indentations 75 and 76 for insertion therein and into the second channel. Second spring piece 71 is released with opposite ends 78 and 79 expanding and inserting into respective indentations 75 and 76 of the second channel for circumferentially ligating between the two pieces vessel 173 positioned in longitudinal channel 73.

Figure 11:
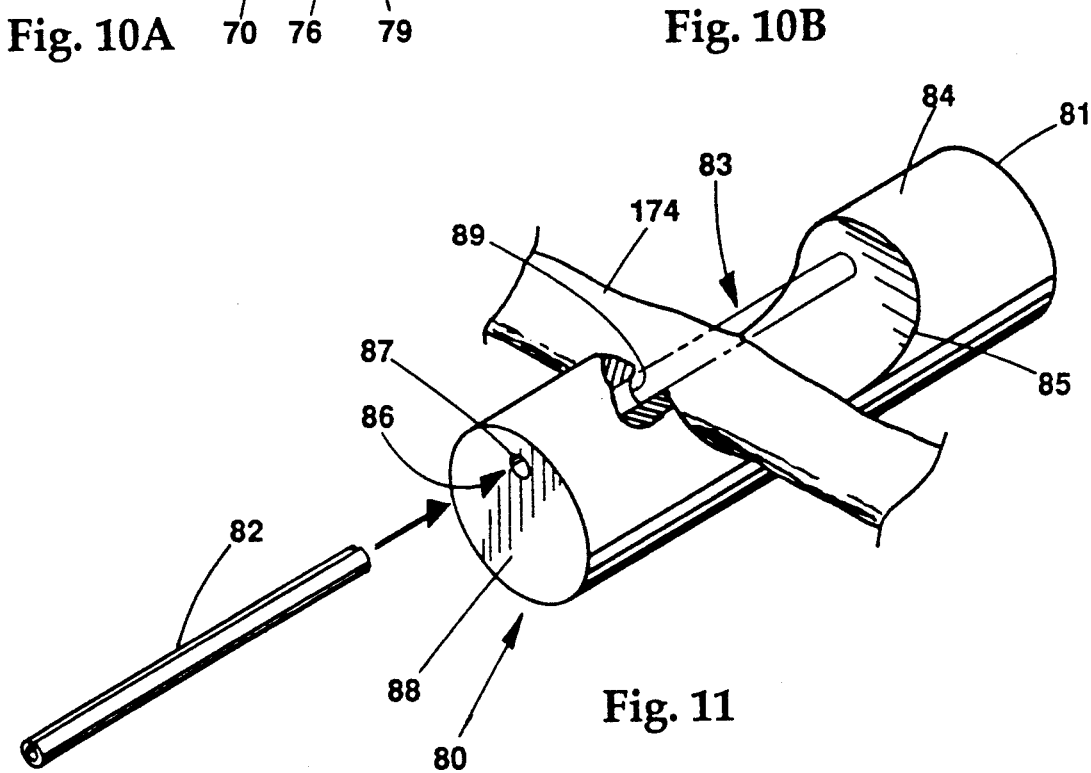
FIG. 11 depicts a further aspect of the two-piece surgical ligating clip of the present invention.

Depicted in FIG. 11 is a pictorial view of two-piece surgical ligating clip 80 comprising first piece 81 and second piece 82 separate from the first piece for ligating between the two pieces vessel 174 positioned in first channel 83 of the first piece. Surgical ligating clip 80 represents a further aspect of the present invention. First piece 81 has an outer surface 84 of which first channel 83 includes opening 85 in the outer surface thereof. The first piece also includes second channel 86 that communicates with first channel 83 as shown. The first piece includes an elongated member, such as a cylindrical rod, having first channel 83 formed therein in a well-known manner transverse to the longitudinal axis of the elongated member rod. Second channel 86 is formed parallel to the longitudinal axis of the rod by drilling a hole in a well-known manner through end 88 of the rod and into first channel 83. Second piece 82 comprises a well-known expansion pin with one end insertable through first opening 87 of second channel 86 and out second opening 89 of the second channel and at least partially into first channel 83. Vessel 174 is positioned in first channel 83, and second piece pin 82 is inserted through second channel 86, out opening 89, and at least partially into first channel 83 over the vessel positioned in the first channel. As shown by the phantom lines, the second piece pin can be extended entirely across the first channel to engage the face of the first channel for a complete circumferential enclosure of vessel 174 in first channel 83.

Figure 12:
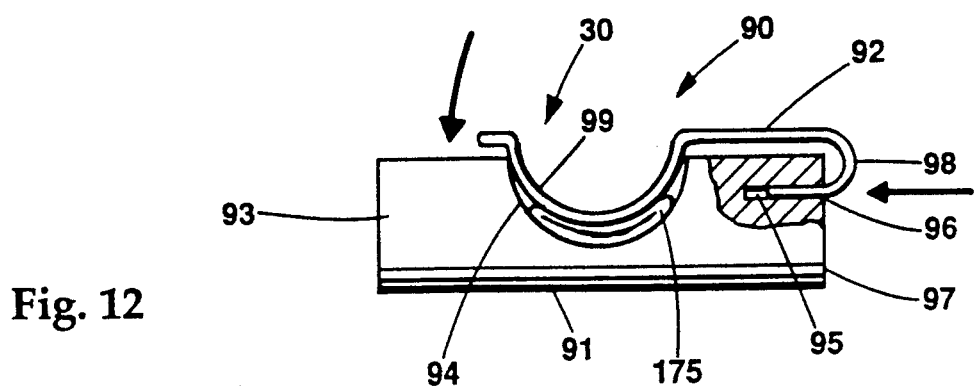
FIG. 12 depicts a still further aspect of the two-piece surgical ligating clip of the present invention and a variation of the clip of FIG. 11.

Depicted in FIG. 12 is a partially sectioned side view of two-piece surgical ligating clip 90 including first elongated member piece 91 and second piece 92, which represent a still further aspect of the present invention and a variation of the two-piece surgical ligating clip of FIG. 11. First piece 91 has an outer surface 93, and a first preformed channel 30 including first opening 94 in outer surface 93. The first piece also includes second preformed channel 95 that is transverse to, but does not communicate with, the first channel and includes opening 96 in outer end surface 97. Second piece 92 is a well-known compression pin which is inserted into second channel 95 through opening 96. The second piece includes a hook-shaped end 98 that is inserted into the second channel with opposite curved end 99 extending at least partially into or through first channel 30. Vessel 175 is inserted into first channel 30, with the second piece being then inserted into second channel 95 with curved end 99 of the second piece positioned over the vessel and across first channel 30 for ligating between the two pieces vessel 175 positioned in first channel 30.

Figure 13:
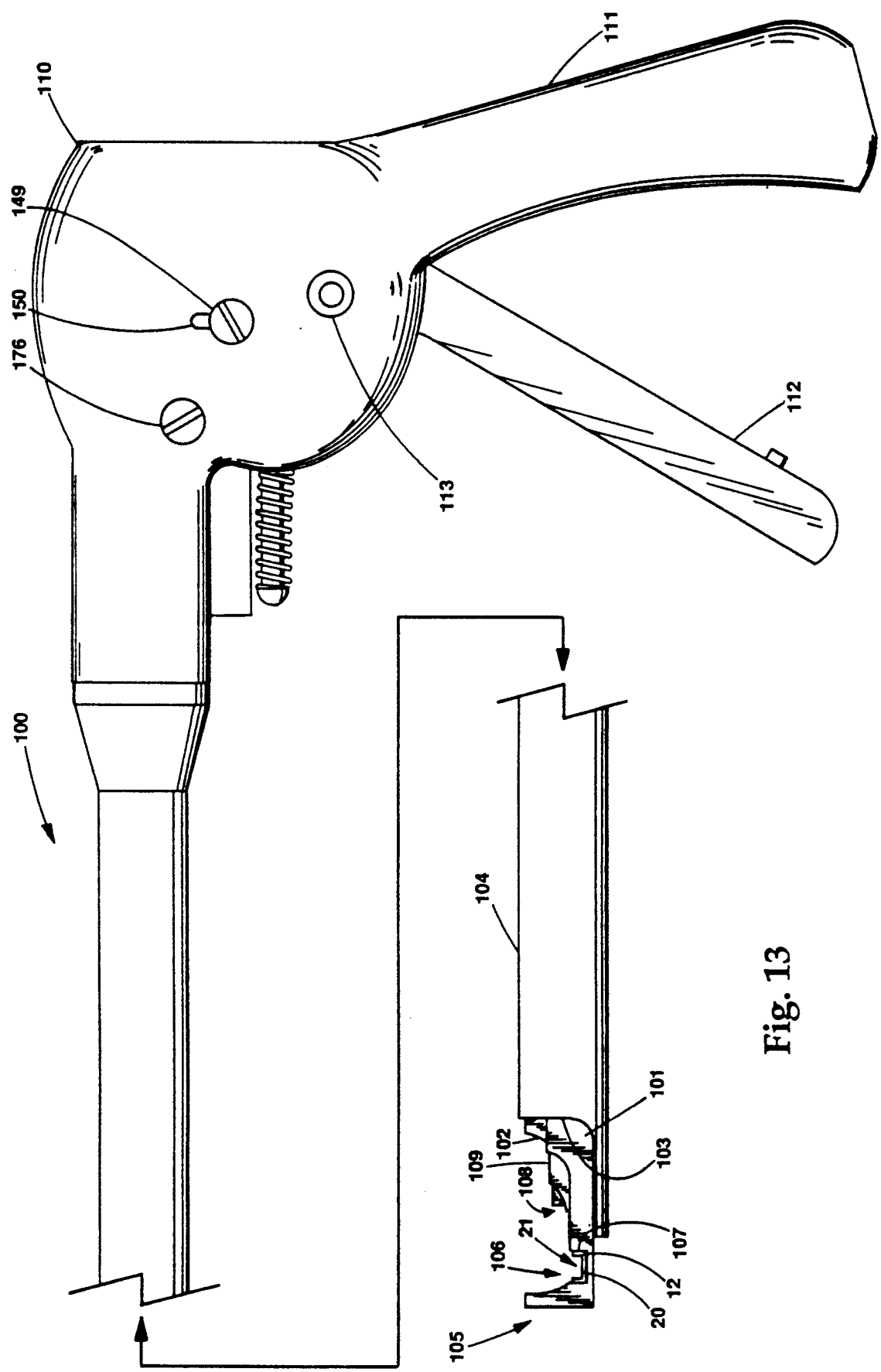
FIG. 13 depicts a side view of the applicator of the present invention for applying the two-piece surgical ligating clip to a vessel.

Depicted in FIG. 13 is a side view of an illustrative applicator 100 for circumferentially ligating a vessel with the two-piece surgical ligating clip 10 (only first piece tube 12 thereof shown) of FIG. 1. The preferred embodiment of applicator 100 includes housing 101 and insertion mechanism 102 both positioned within passage 103 of outer sleeve 104. The housing includes a distal end 105 and a vessel channel 106 positioned longitudinally within the housing about distal end 105. The vessel channel includes a vessel access opening 107 communicating with second channel 21 and in turn openings 19 (not shown) and 20 of first piece tube 12 positioned within vessel channel 106. Depicted in an initial position, insertion mechanism 102 is positioned within longitudinally extending guide channel 109 of housing 101 and includes a distal end 108. Insertion mechanism 102 also includes a delivery position when positioned about distal end 105 of the housing for positioning a second tube of the clip into a passage of first piece tube 12 and circumferentially ligating a vessel (not shown) between the two tubes when the vessel is positioned through second channel 21 of the first piece tube.

Applicator 100 further comprises a handle 110 connected to outer sleeve 104, which includes grip 111 and trigger 112 pivotedly connected to the grip with pin 113. The proximal end of housing 101 is detachably connected to handle 110 via commercially available lock pin 176. Trigger 112 has a plurality of positions with respect to grip 111 and is shown in FIG. 13 in a released position. To ligate a vessel positioned in second channel 21 of first tube 12 and vessel channel 106 of housing 101, an attending physician will grasp the grip and trigger in his hand and pull the trigger toward the grip to urge insertion mechanism 102 toward distal end 105 of the housing and position the second tube in a passage of first tube 12. When a vessel is ligated, the physician releases the trigger which has engaged on the clip ejector of the applicator to eject the clip. Release mechanism pin 149 is slid upward in handle slot 150 to disengage the clip ejector from the trigger.

Figure 14A:
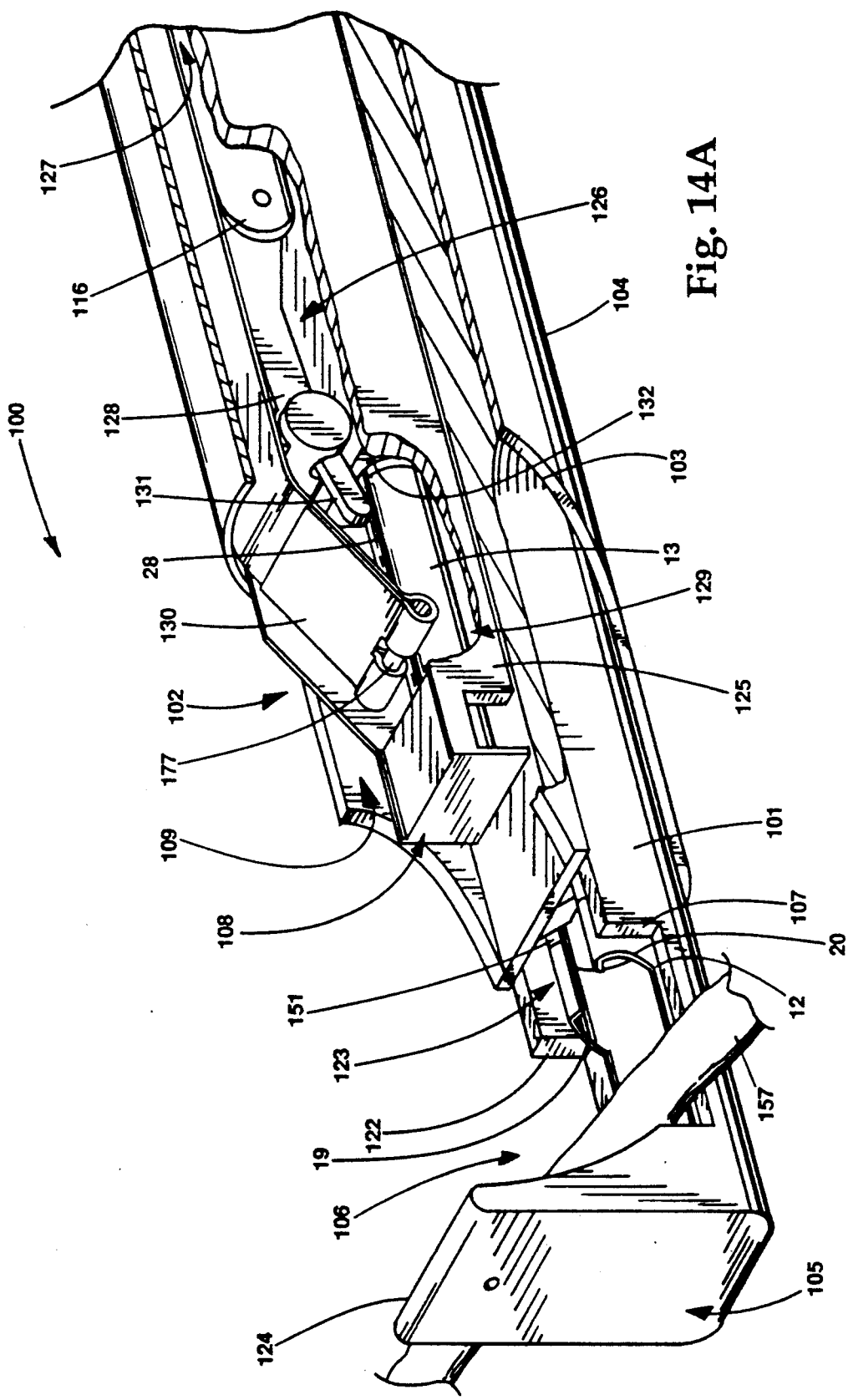
FIG. 14A depicts an enlarged, partially-sectioned pictorial view of the distal end of the applicator of FIG. 13.

Depicted in FIG. 14A is an enlarged, partially sectioned pictorial view of the distal end of applicator 100 of FIG. 13. As shown, main housing 101 includes vessel channel 106 with opposite end vessel access openings 107 and 122 on opposite sides of first tube passage 123. First tube 12 is positioned transversely through vessel channel 106 and longitudinally in first tube passage 123. As depicted, first tube openings 19 and 20 communicate with vessel channel 106 and vessel access openings 107 and 122. Positioned at distal end 105 of the housing and the distal end of first tube 123 is stop 124 for fixedly positioning longitudinally first tube 12 in first tube passage 123.

Housing 101 extends longitudinally through passage 103 of outer sleeve 104 and is connected to handle 110 as depicted in FIG. 13. Extending longitudinally through main housing 101 is guide channel 109 of which insertion mechanism 102 is slidably positioned. Insertion mechanism includes carriage 125 and insertion projection 126 slidably extendable through insertion projection channel 127 of the carriage. Insertion projection 126 includes push rod 116 and clamping arm 128 pivotedly connected to the distal end of the push rod. Positioned near distal end 108 of insertion mechanism 102 and in particular carriage 125 is delivery passage 129 with second piece tube 13 positioned therein with longitudinal slot 28 of the second tube oriented in a longitudinal position as shown.

Insertion mechanism 102 further includes deflection arm 130 longitudinally positioned about and across delivery passage 129 for guiding clamping arm 128 when urged toward the distal end of the carriage. Deflection arm 130 is fixedly positioned about and across the delivery passage with anchor pin 177 as shown. When so urged, finger 131 extending from clamping arm 128 extends through longitudinal slot 28 of the second tube to engage the inner surface of second piece tube wall. When second tube 13 is securably positioned in the first passage of first tube 12, a plurality of second tubes (not shown) are urged through second tube passage 132 toward the distal end of the insertion mechanism. When vessel 157 is ligated between first tube 12 and second tube 13 and subsequently ejected from vessel channel 106, a plurality of first tubes 151 are similarly urged through first tube passage 123 toward distal end 105 of the main housing. As the plurality of first tubes are urged toward distal end 105, the distal-most first tube of the plurality engages stop 124.

Figure 14B:
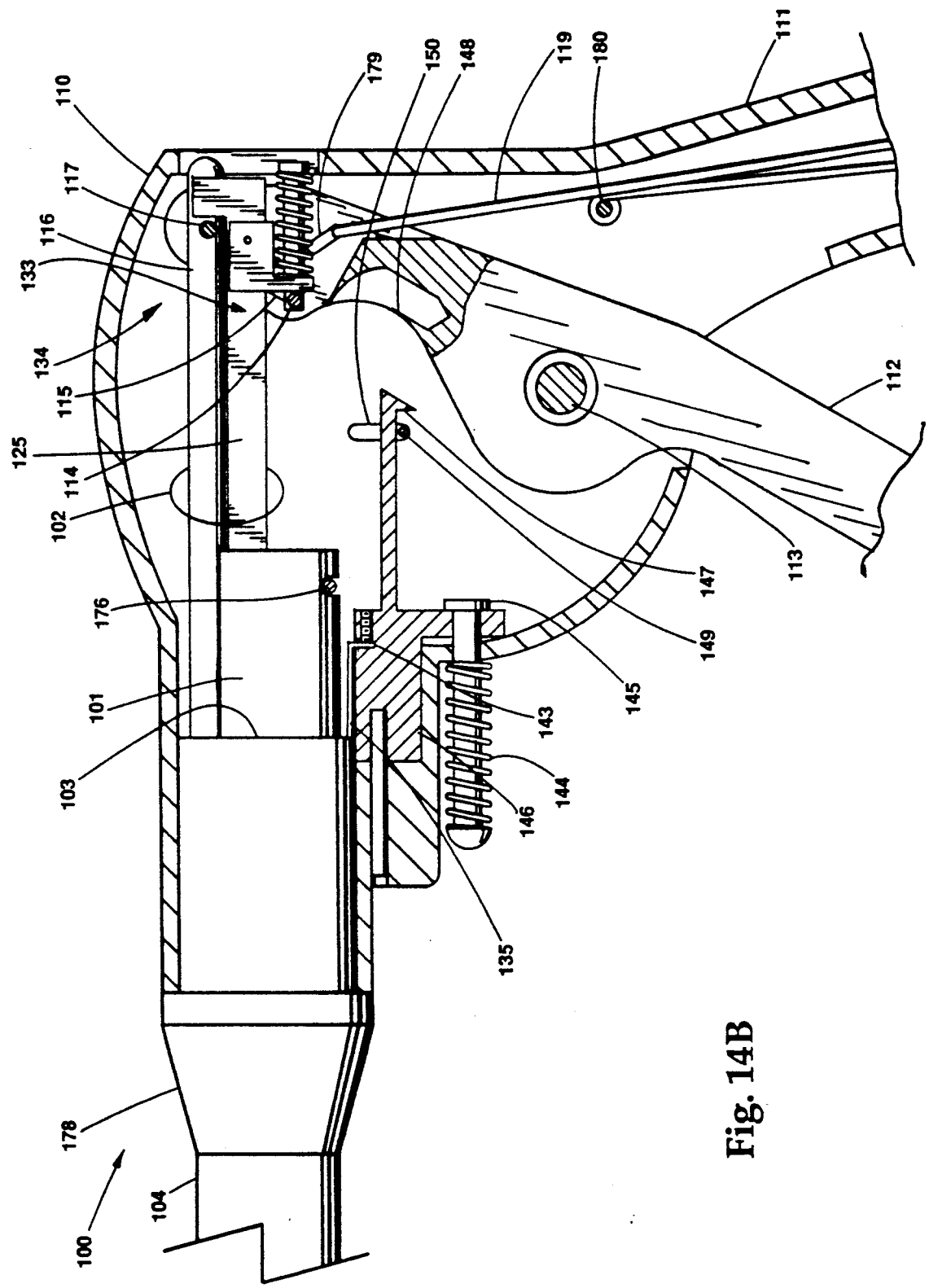
FIG. 14B depicts an enlarged, partially-sectioned side view of the handle of the applicator of FIG. 13.

Depicted in FIG. 14B is an enlarged, partially sectioned side view of handle 110 of applicator 100 of FIG. 13. Not only is trigger 112 pivotedly connected to grip 111 via pin 113, the trigger is also pivotedly and slidably connected to insertion mechanism 102 about proximal end 133 thereof with pin 114 sliding in elongated slot 115 of the trigger. The trigger is further pivotedly and slidably connected to push rod 116 about proximal end 134 thereof with pin 117 sliding in elongated slot 118 (shown in FIG. 25) of the trigger. Handle 110 further includes clip ejector spring 144 connected to proximal end 143 of clip ejector 135 via spring rod 145 and slidable member 146. Slidable member 146 also includes hooked-end finger 147 extending proximally therefrom for engaging trigger catch 148. The handle also includes release mechanism pin 149 positioned in handle slot 150, which is transversely positioned to the finger, and engaging hooked-end finger 147 for releasing the finger from trigger catch 148. As a result, the proximal end of the clip ejector is released with pin 149 from the trigger when the clip ejector is in the ejected position. When so released, compressed clip ejector spring 144 urges clip ejector 135 to the relaxed position as shown. As also shown, the proximal end of main housing 101 is detachably connected to handle 110 via lock pin 176. The proximal ends of main housing 101 and insertion mechanism extend proximally from passage 103 of outer sleeve 104. Outer sleeve 104 is connected to handle 110 via well-known hub 178. The trigger is urged to the released position (as shown) with spring 119 connected to trigger slot 179 and grip pin 180.

Figure 15:
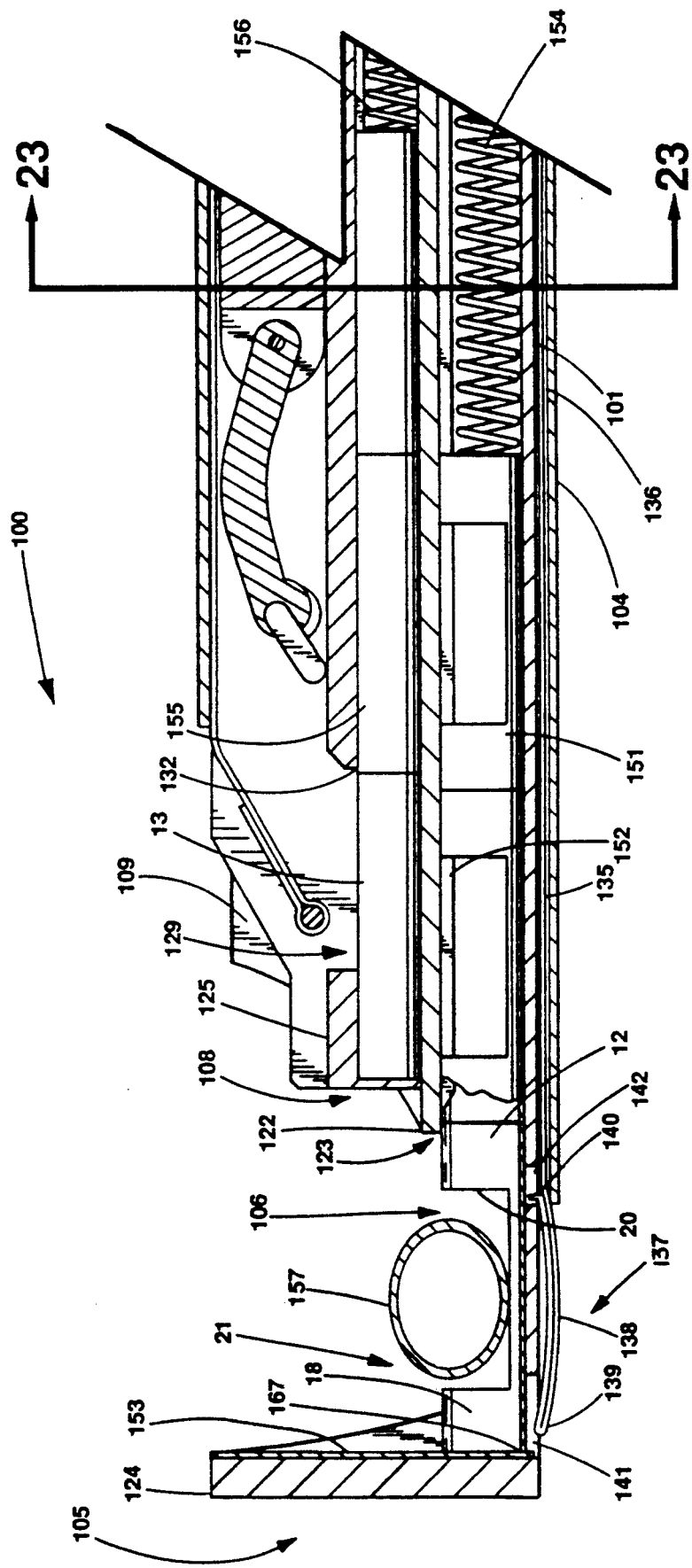
FIG. 15 depicts a partially-sectioned side view of the distal end of the applicator of FIG. 14A with a vessel positioned therein.

Depicted in FIG. 15 is an enlarged, partially-sectioned side view of the distal end of FIG. 14A. Applicator 100 further includes clip ejector 135 positioned between outer sleeve 104 and main housing 101 and longitudinally in ejector channel 136 that extends longitudinally in main housing 101. As depicted, clip ejector 135 is in a relaxed position. Distal end 137 of the clip ejector has folded-back portion 138. Distal end 139 and proximal end 140 of folded-back portion 138 extend respectively into distal opening 141 and proximal opening 142 positioned at the bottom of vessel channel 106 and first tube passage 123. Clip ejector 135 also has an ejected position when distal end 137 of the ejector and distal end 139 of folded-back portion 138 are urged into ejector channel 136. As a result, proximal end 140 of folded-back portion 138 engages proximal opening 142 and is urged therethrough to engage first piece tube 12 positioned in vessel channel 106 and first passage 123. When the clip ejector is fully positioned in the ejected position, proximal end 140 of folded-back portion 138 engages and pushes first piece tube 12 out of vessel channel 106 and first passage 123. When in the fully ejected position, the proximal end of clip ejector 135 is releasably connected to the trigger.

As further depicted in FIG. 15, stop 124 is positioned at distal end 105 of main housing 101 for engaging distal end 108 of carriage 125 when the carriage is in a delivery position. To orient plurality 151 of first piece tubes in first tube passage 123 as shown, the applicator further includes narrow positioning projection 152 extending into first tube passage 123 of housing 101 and the longitudinal slot or opening in each first tube of the plurality positioned in the passage. Similarly, to maintain the orientation of first piece tube 12 when positioned in vessel channel 106, stop 124 includes flexible positioning projection 153 extending therefrom and into vessel channel 106 and first tube passage 123 of applicator 100 and passage 18 and notch 167 of first tube 12. When first piece tube 12 is ejected from vessel channel 106 and first passage 123, first tube spring 154 positioned in first passage 123 communicates with and engages the plurality of first piece tubes, urging them toward vessel channel 106. Second piece tube 13 is positioned in delivery passage 129 and second tube passage 132 of carriage 125. Also positioned in second tube passage is plurality 155 of second piece tubes with second tube spring 156 urging the plurality of second piece tubes toward delivery passage 129. As previously indicated, when the trigger is in a released position, carriage 125 of insertion mechanism 102, which is slidably positioned in guide channel 109 of main housing 101, is also in a released position as depicted in FIG. 15.

Depicted in FIG. 23 is an enlarged, cross-sectional view of applicator 100 of FIG. 15 taken along the line 23—23. As shown, tubular outer sleeve 104 contains main housing 101 with insertion mechanism 102 slidably positioned in guide channel 109 of the main housing. Insertion mechanism 102 includes carriage 125 with second tube passage 132 containing plurality 155 of second piece tubes longitudinally positioned therein and insertion projection channel 127 containing push rod 116. Deflection arm 130 caps insertion projection channel 127. Main housing 101 includes first tube passage 123 containing plurality 151 of first piece tubes. Positioning projection 181 extends into second tube passage 132 and slot opening 28 of a second tube to maintain the orientation of the plurality as they are urged toward the distal end of the carriage. Similarly, positioning projection 12 extends into first tube passage 123 and longitudinal slot 17 of a first tube to maintain the orientation of the tube in the passage as it is urged toward the distal end of the applicator. Main housing 101 comprises a U-shaped guide channel insert 166 positioned in guide channel 109 with positioning projection 152 extending from the bottom thereof and into first tube passage 123. This guide channel insert is formed of, for example, a DELRIN ™ polymer material, and is utilized with main housing 101 to permit assembly of the applicator with the various passages and channels extending longitudinally therethrough. At the bottom of main housing 101 is clip ejector channel 136 extending longitudinally therethrough with clip ejector 135 positioned therein.

Depicted in FIG. 24 is an enlarged, partially-sectioned pictorial view of the underside of the distal end of applicator 100 of FIG. 15. In this figure, a better view of clip ejector 135 is shown positioned in a relaxed position in openings 141 and 142 at the bottom of vessel channel 106 in main housing 101. When clip ejector 135 is pulled proximally in channel 136, distal end 137 of the ejector engages the distal end of outer sleeve 104, thereby forcing folded-back portion 138 and proximal end 140 thereof through opening 142 to eject a clip in vessel channel 106. Also note that flexible projection 153 extends into access channel 106 when a first piece tube is not in the access channel.

With a basic understanding of the structure of two-piece surgical ligating clip 10 and applicator 100, the method of ligating a vessel utilizing the two-piece surgical clip and the applicator will now be described. The two-piece surgical ligating clip and applicator therefor is preferably utilized in a minimally invasive surgical procedure. However, the two-piece clip and applicator can be used equally as well in any open, invasive surgical procedure. In a minimally invasive surgical procedure, one or more surgical access sheaths are percutaneously inserted into a cavity of a patient. These access sheaths typically have an inside diameter ranging from 5-10 mm. An endoscope is commonly inserted through one of these access sheaths to provide visual monitoring of the insufflated cavity. The other access sheaths, as well as the endoscope, are utilized for inserting other minimally invasive surgical instruments therethrough and into the cavity for manipulating organs, ducts, tissue and the like contained therein. The outer sleeve of the applicator of the present invention is nominally less than the inside diameter of at least one of these access sheaths for insertion therethrough and into the cavity. The length of the outer sleeve and main housing is nominally 30 cm for insertion through an access sheath and for positioning the distal end of the main housing about the vessel to be ligated. The attending physician will prepare a vessel or duct to be ligated by stripping away any connective tissue therefrom. As depicted in FIGS. 14A and 15, the distal end of applicator 100 is positioned about vessel 157 with the vessel positioned through vessel access openings 107 and 122 at the opposite ends of vessel channel 106 and on opposite sides of the distal end of first tube passage 123. First piece tube 12 is transversely positioned across vessel channel 106 and longitudinally positioned in first tube passage 123. Vessel 157 also extends through second channel 21 of first piece tube 12 with openings 19 and 20 of the second channel positioned at the opposite ends thereof. First tube openings 19 and 20 communicate with vessel access openings 107 and 122, respectively. The vessel is also positioned in passage 18 of the first piece tube into which second piece tube 13 of the clip will be eventually inserted to circumferentially ligate the vessel.

Figure 16:
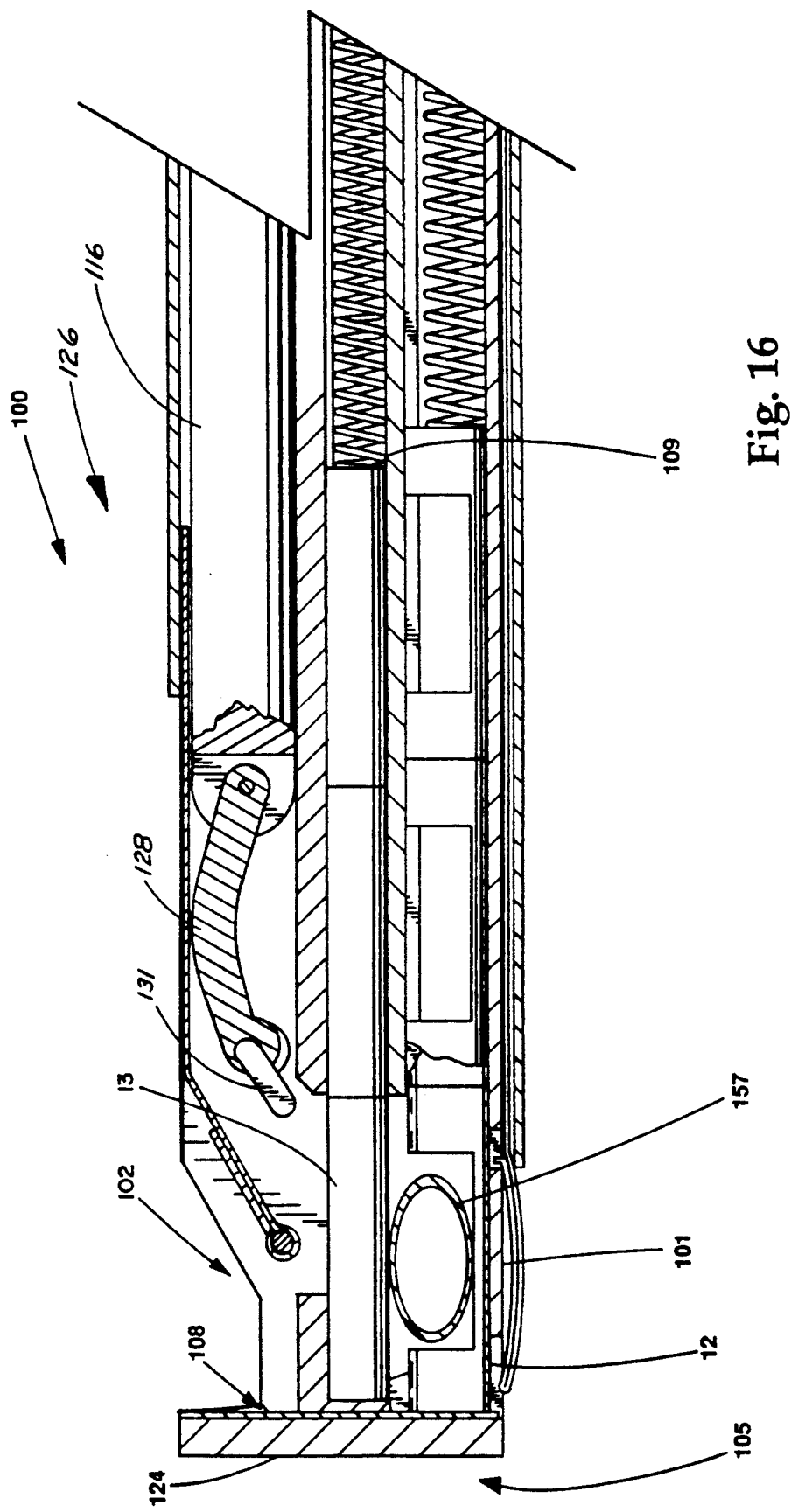
FIG. 16 depicts a partially-sectioned side view of the distal end of the applicator of FIG. 15 with the insertion mechanism thereof in a delivery position.

When vessel 157 is positioned through first tube openings 19 and 20 and vessel access openings 107 and 122, the physician grasps handle 110 of the applicator and squeezes trigger 112 toward grip 111 as depicted in FIG. 14B. As trigger 112 is pulled, insertion mechanism 102 slides in guide channel 109 toward distal end 105 of main housing 101. When distal end 108 of insertion mechanism 102 engages stop 124 of the main housing, the insertion mechanism is in the delivery position with second piece tube 13 positioned directly above first piece tube 12 as depicted in FIG. 16. The physician continues to squeeze trigger 112 toward grip 111 of the applicator handle. As previously described with respect to FIG. 14B, trigger 112 is connected to proximal end 134 of push rod 116 and proximal end 133 of carriage 125. However, the connection of the trigger to carriage 125 is relaxable when the carriage is in the delivery position as described with respect to FIG. 17.

Figure 17:
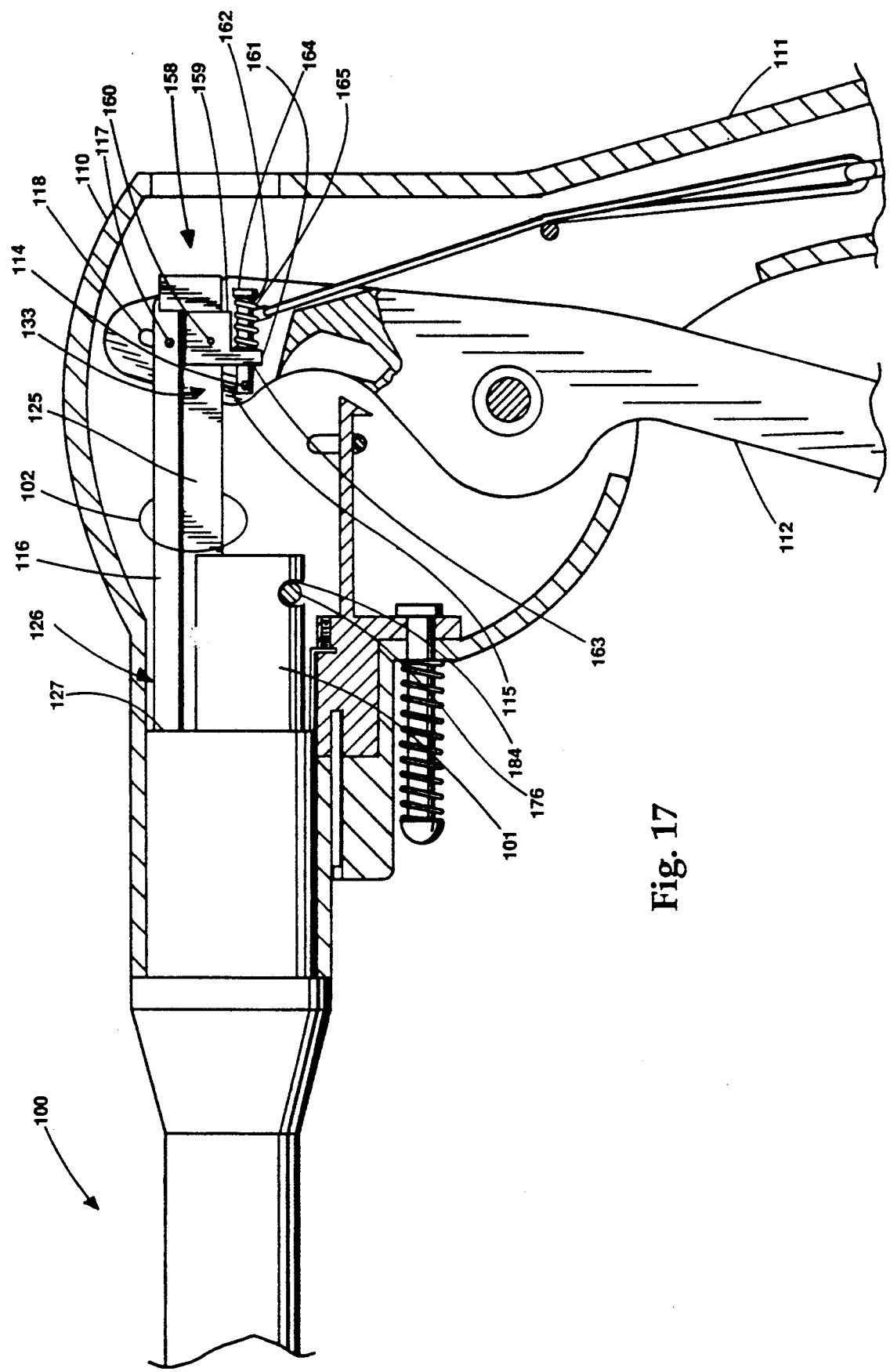
FIG. 17 depicts an enlarged, partially-sectioned side view of the handle of the applicator of the present invention in a delivery position.
Figure 25:
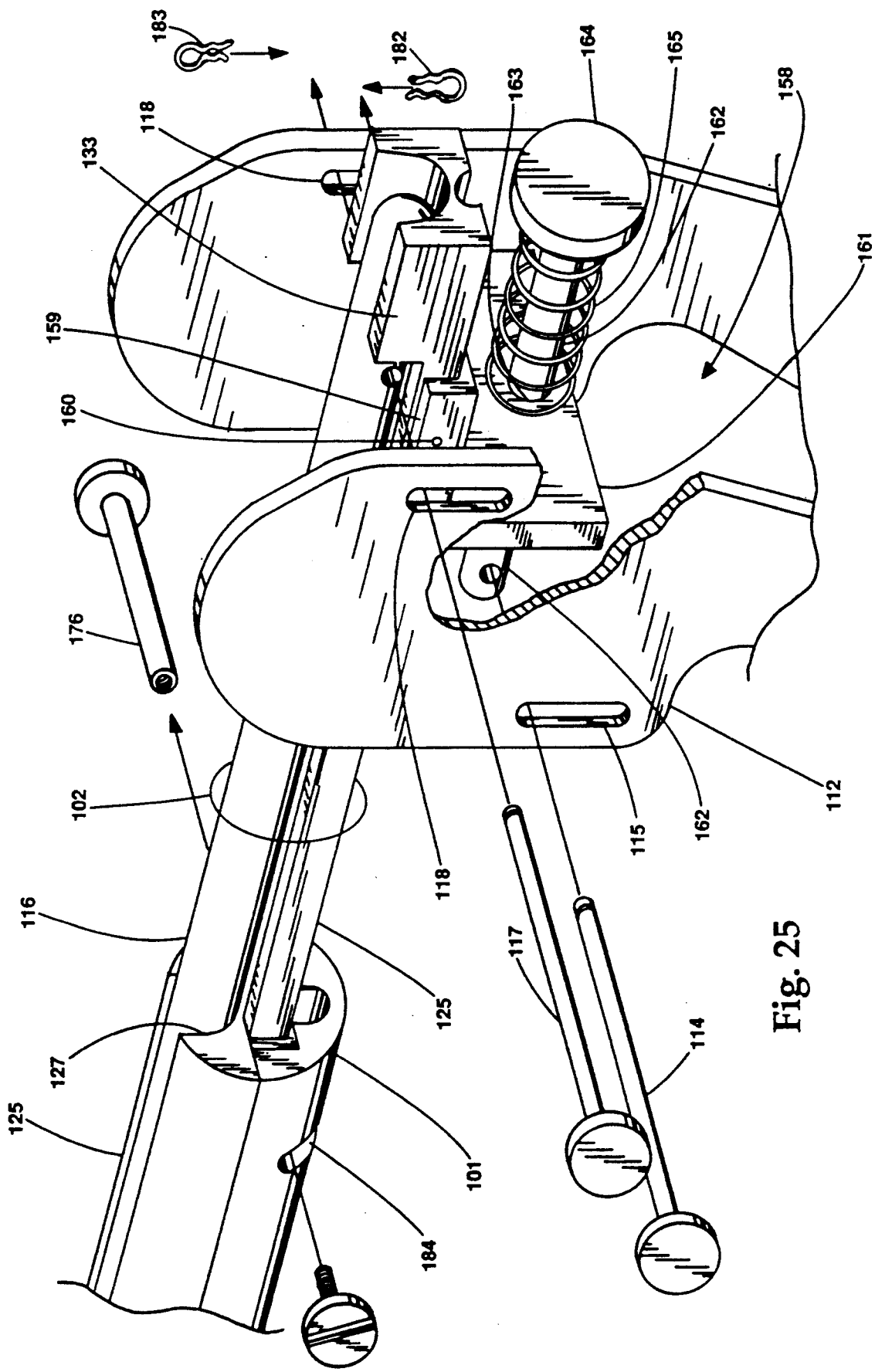
FIG. 25 depicts an enlarged, partially-sectioned, pictorial view of the connection of the insertion mechanism and trigger of the applicator of FIG. 17.

Depicted in FIG. 17 is an enlarged, partially-sectioned side view of handle 110 of applicator 100 with trigger 112 and insertion mechanism 102 in the delivery position. Depicted in FIG. 25 is an enlarged, partially-sectioned pictorial view of the connection of insertion mechanism 102 and trigger 112 of FIG. 17. Proximal end 133 of carriage 125 is relaxably connected to trigger 112 via spring relax mechanism 158. Spring relax mechanism 158 includes U-shaped cradle bracket 159 connected to proximal end 133 of carriage 125 via well-known fastener 160. Cradle bracket 159 has a downwardly extending flange 161 through which spring rod 162 passes through cradle flange aperture 163. The distal end of spring rod 162 is transversely connected to pin 114 which is slidably contained in elongated slot 115. The proximal end of spring rod 162 includes end cap 164 for compressing carriage relax spring 165 positioned around the spring rod between end cap 164 and cradle bracket flange 161. As the physician continues to squeeze trigger 112 toward grip 111, push rod 116 continues to slide forward in insertion projection channel 127 of carriage 125. Push rod 116 is pivotedly connected to trigger 112 via pin 117 positioned in trigger elongated slot 118. Pins 114 and 117 are held in position by clips 182 and 183. Pin 176 secures main housing 101 to the handle by positioning the pin through the handle and main housing slot 184. As push rod 116 is urged distally forward, trigger 112 also pulls spring rod 162 forward, compressing carriage relaxation spring 165 between end cap 164 and cradle flange 161, thereby relaxing the connection between trigger 112 and carriage 125. As a result, carriage 125 as depicted in FIG. 16 remains in a fixed position with the distal end thereof engaging stop 124 of the main housing, while push rod 116, clamping arm 128, and finger 131 of insertion projection 126 continue to be urged distally forward.

Figure 18:
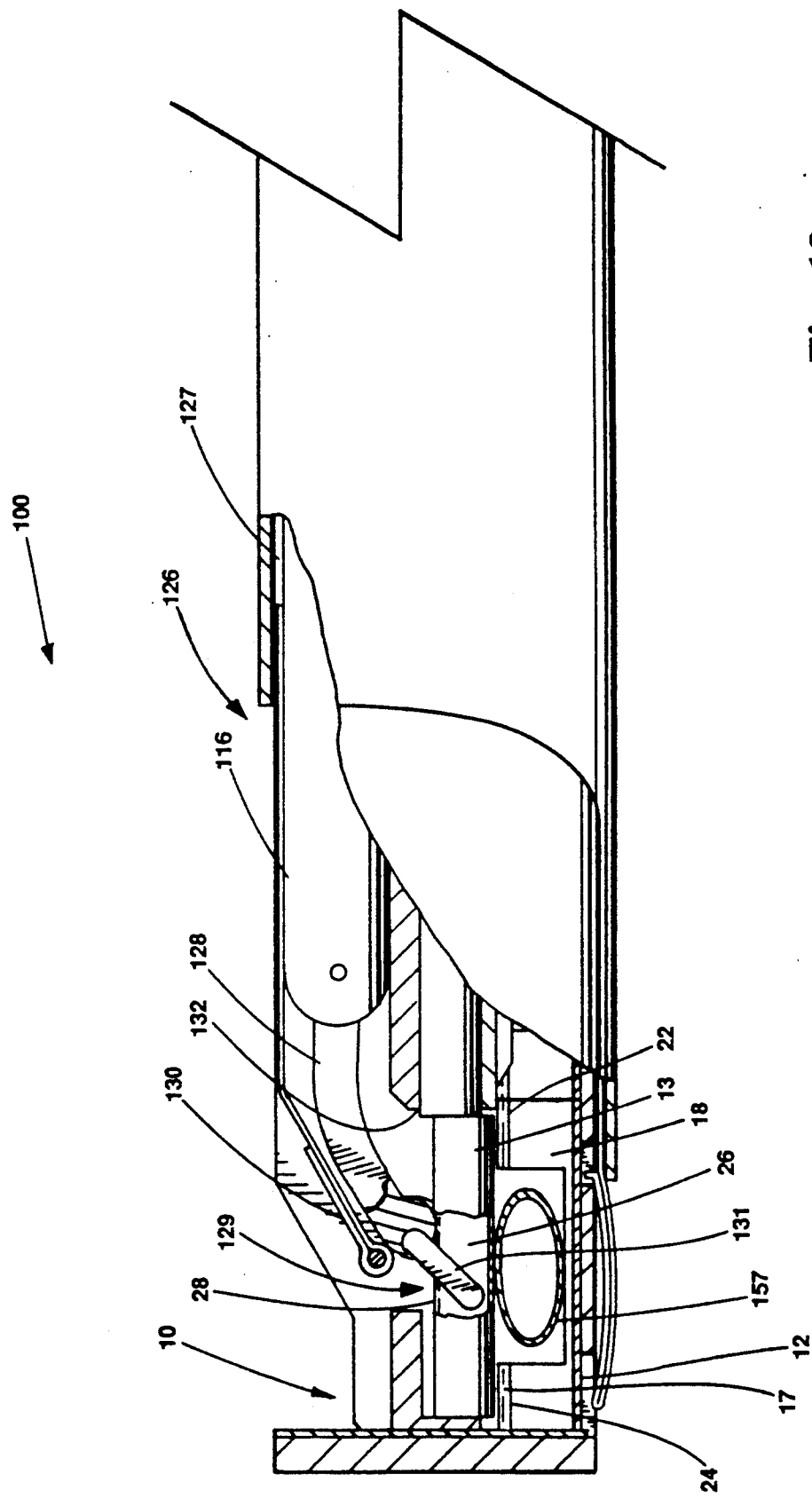
FIG. 18 depicts an enlarged, partially-sectioned side view of the distal end of the applicator of FIG. 16 with the clamping arm thereof positioning a second tube into the passage of the first tube of the surgical ligating clip of the present invention.

Depicted in FIG. 18 is an enlarged, partially-sectioned side view of the distal end of applicator 100 of FIG. 16 with clamping arm 128 engaging deflection arm 130. As push rod 116 is urged distally forward in insertion projection channel 127, clamping arm 128 engages the distal end of deflection arm 130 and second piece tube 13. Deflection finger 131 extending from clamping arm 128 extends into passage 26 of second piece tube 13 through longitudinal slot 28 and engages the inner surface of the tube wall opposite the longitudinal slot. As the physician continues to squeeze the trigger, deflection arm 130 cams clamping arm 128 further through delivery passage 129 forcing second piece tube 13 downwardly from the delivery passage and second tube passage 132 on top of vessel 157 and into longitudinal slot 17 of the first tube. As the push rod is urged distally forward, second tube 13 is further positioned into longitudinal slot 17 of first piece tube 12 to engage tangs 22—25. As second piece tube 13 is pushed into first passage 18 of first piece tube 12, longitudinal slot 17 expands and second piece tube 13 compresses to pass through longitudinal slot 17 and into first tube passage 18, thereby compressing and ligating vessel 157 between the two tubes of clip 10.

Figure 19:
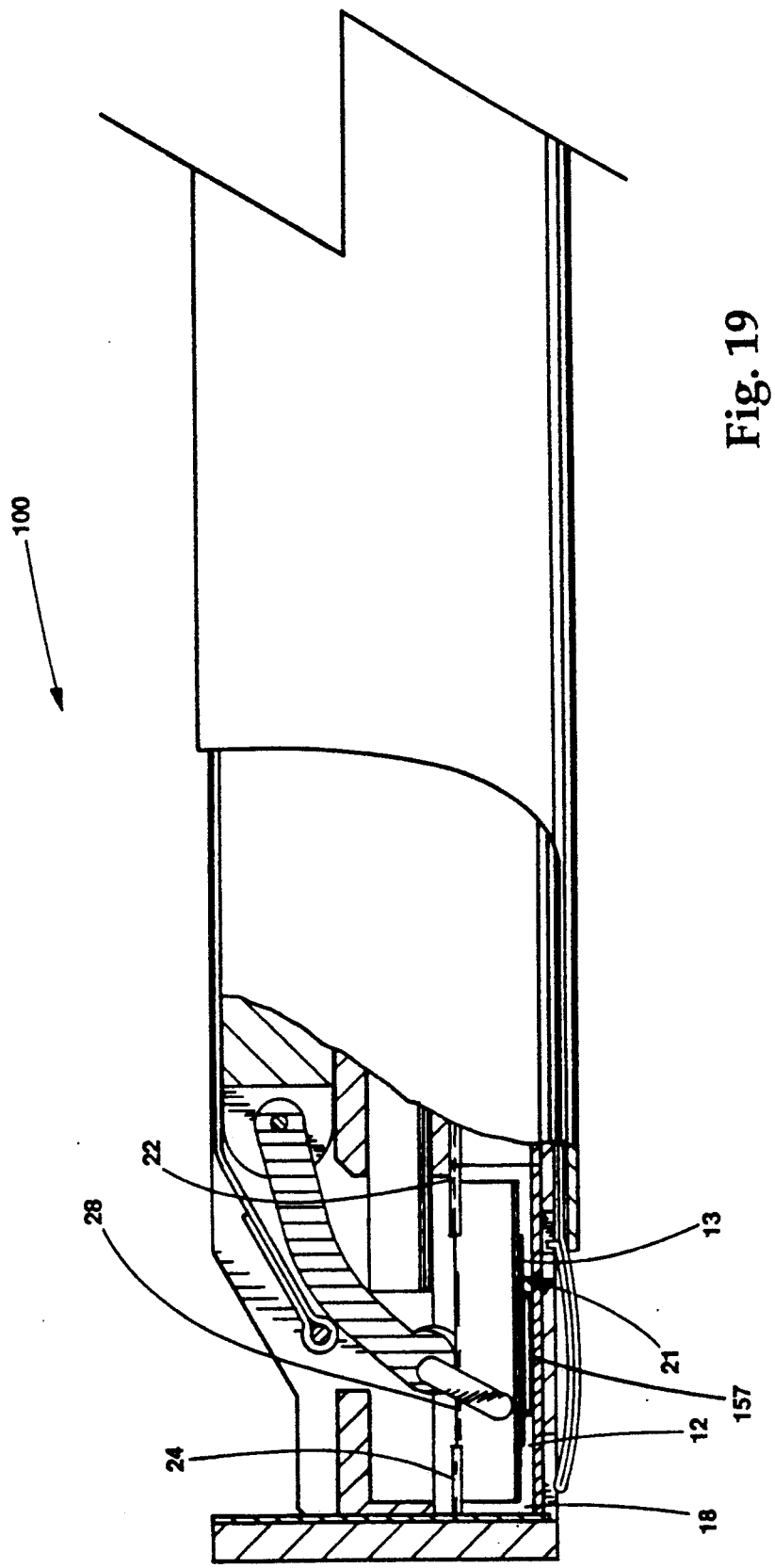
FIG. 19 depicts an enlarged, partially-sectioned side view of the distal end of the applicator of FIG. 18 with the clamping arm thereof securably positioning the second piece tube in the passage of the first piece tube.

Depicted in FIG. 19 is an enlarged, partially-sectioned side view of applicator 100 of FIG. 18 with second piece tube 13 securably positioned longitudinally in passage 18 and transversely across second channel 21 of first tube 12. Vessel 157 is circumferentially ligated between the two tubes which are securely positioned together with the edges of longitudinal slot 28 of second piece tube 13 engaging tangs 22—25 of first piece tube 12. An end view of second piece tube 13 securably positioned in passage 18 and across channel 21 of first piece tube 12 and circumferentially ligating vessel 11 is depicted in FIG. 3.

Figure 20:
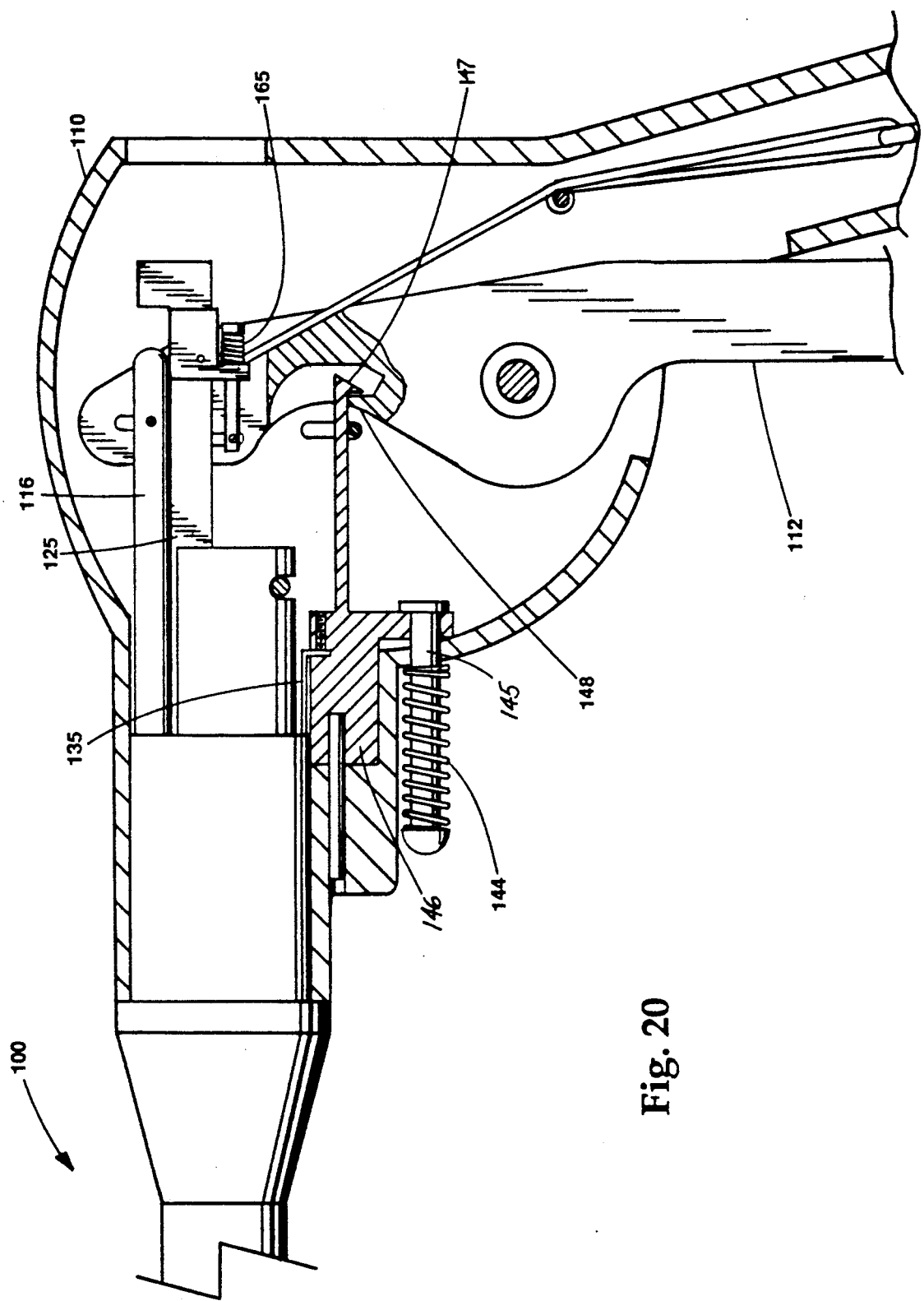
FIG. 20 depicts an enlarged, partially-sectioned side view of the applicator trigger in a full delivery position.

Depicted in FIG. 20 is an enlarged, partially-sectioned, side view of handle 110 of applicator 100 of FIG. 19 with trigger 112 in a full delivery position. Hooked-end finger 147 engages trigger catch 148. As a result, clip ejector 135 is releasably connected to trigger 112. Also note the compression of carriage relaxation spring 165 with the trigger in a full delivery position. As previously described with respect to FIG. 16, this relaxable connection allows push rod 116 to be urged distally after carriage 125 in a delivery position engages stop 124. As the trigger is subsequently released by the physician, clip ejector 135, spring rod 145, slidable member 146, and hooked-end 147 are pulled proximally as clip ejector spring 144 is compressed.

Figure 21:
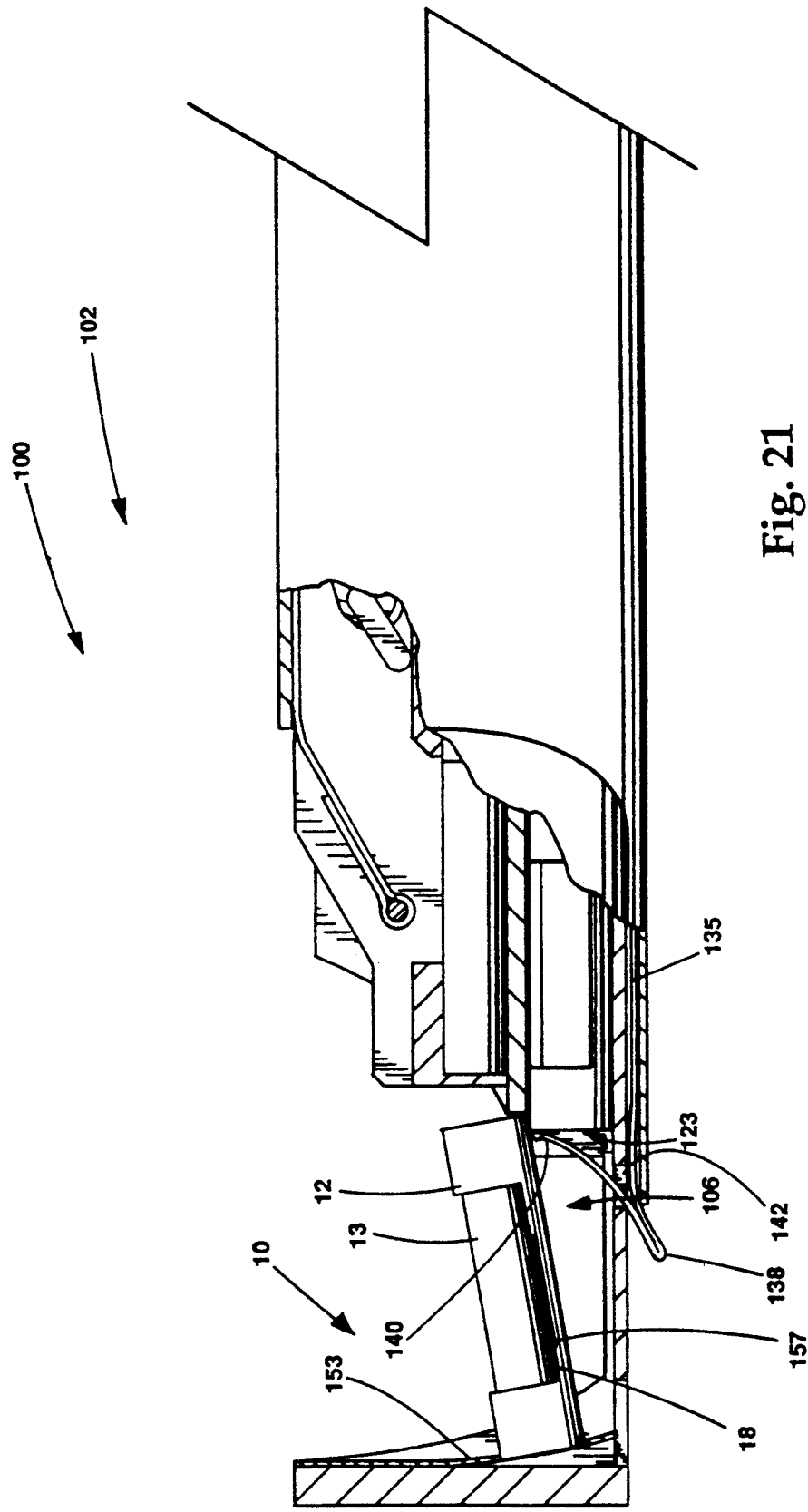
FIG. 21 depicts an enlarged, partially-sectioned side view of the distal end of the applicator of FIG. 19 with the surgical ligating clip applied to a vessel and being ejected from the applicator.
Figure 22:
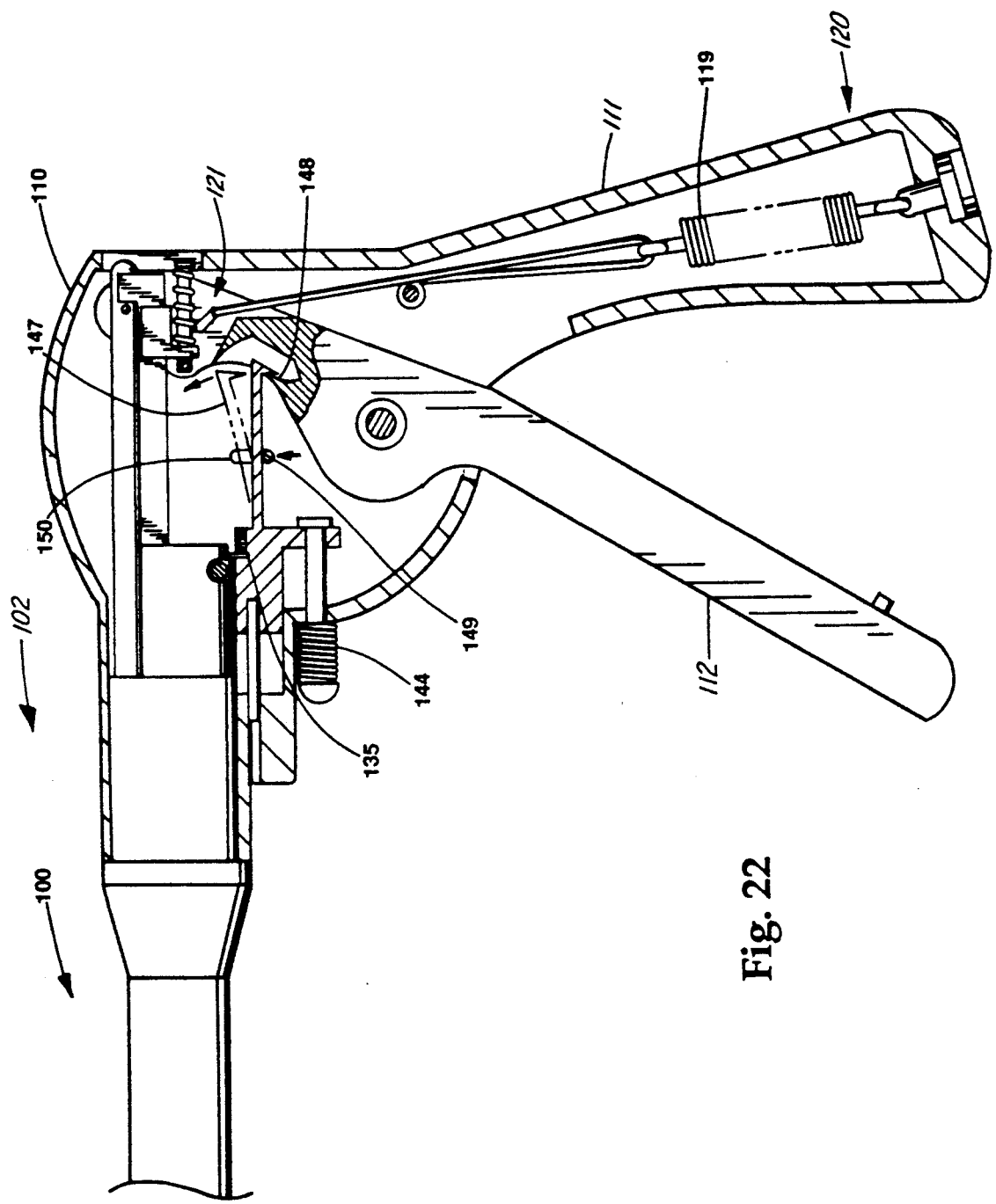
FIG. 22 depicts an enlarged, partially sectioned side view of the applicator handle of FIG. 19 with the clip ejector being released to return to a relaxed position.

Depicted in FIG. 21 is an enlarged, partially-sectioned side view of the distal end of applicator 100 of FIG. 19 with ligated vessel 157 being ejected from vessel channel 106 and first tube passage 123. After second piece tube 13 has been securably positioned in passage 18 of first piece tube 12 thereby circumferentially ligating vessel 157, the physician releases the trigger. Insertion mechanism 102 is pulled back to the released position by trigger spring 119 as depicted in FIG. 14A and FIG. 22. As previously described, hooked-end finger 147 engages trigger catch 148 when the trigger is pulled to the delivery position. When the trigger is released by the physician, proximal end 143 of clip ejector 13 is pulled proximally compressing clip ejector spring 144. As depicted in FIG. 21, proximal end 140 of folded-back portion 138 engages proximal opening 142 and first piece tube 12 and pushes clip 10 and the ligated vessel out of vessel channel 106 and first tube passage 123 as shown. As previously described, clip ejector 135 is now in the ejected position.

Depicted in FIG. 22 is an enlarged, partially-sectioned, side view of handle 110 of applicator 100 of FIG. 19 with clip ejector 135 being released to return to a relaxed position. The physician releases hooked-end finger 147 from trigger catch 148 by lifting release mechanism pin 149 riding in elongated handle slot 150. Clip ejector 135 returns to the relaxed position with the expansion of compressed clip ejector spring 144. As insertion mechanism 102 is returned to the released position and the clip is ejected from applicator 100, springs urge the plurality of first and second piece tubes toward the distal end of the applicator in the first and second tube passages. Spring 119 is connected between proximal end 120 of grip 111 and distal end 121 of trigger 112, as shown, for urging the trigger to the released position. Applicator 100 is now ready to apply another surgical ligating clip to the same or another vessel.

While the invention has been illustrated and described in detail in the drawings and foregoing description, the same is to be considered as illustrative and not restrictive in character, it being understood that only the preferred embodiment of the surgical ligating clip and several configurations thereof along with the applicator and method of use have been shown and described and that all changes and modifications that come within the spirit of the invention are desired to be protected. In particular, the first and second pieces of the surgical ligating clip may be positioned in sequence in the first piece passage of the main housing with the insertion mechanism positioning the second piece into a channel of the first piece positioned directly in front thereof. Also contemplated is an end insertion of the second piece rather than through the top or side of the first piece. Furthermore, it is contemplated that the first piece may be vertically oriented in the vessel channel of the applicator along with the vertical or horizontal orientation of the second piece for either a side or lateral insertion of the second piece into the passage of the first piece. The applicator of the present invention is contemplated to be designed to particularly insert the second piece of any configuration of the clip into the first piece thereof. It is further contemplated that a plurality of first and second tubes can be loaded into the main housing by either disassembling the main housing and insertion mechanism from the handle and trigger and inserting them therein, or by inserting a clip of these tubes through an aperture in the outer sleeve much like a clip of shells are loaded into a rifle.

We claim:

1. A surgical ligating clip comprising:
a first piece having an outer surface, at least a partially circular cross-sectional shape, a first preformed channel including a first opening in said outer surface, and a second preformed channel communicating with said first channel and including a second opening in said outer surface communicating directly with said first opening; and a second piece separate from said first piece and securably positionable in at least one of said first and second channels through at least one of said first and second openings.

2. The clip of claim 1 wherein said first piece includes a first elongated member.

3. The clip of claim 2 wherein said second piece includes a second elongated member.

4. The clip of claim 1 wherein said first piece comprises a first, at least partially cylindrical tube having an outer wall and a passage extending therein.

5. The clip of claim 4 wherein said first channel includes said passage and said passage has a first predetermined width and wherein said first opening comprises a longitudinal slot in said outer wall of said first tube, said longitudinal slot communicating with said passage and having a second predetermined width less than said first width of said passage.

6. The clip of claim 5 wherein said second piece comprises a second, at least partially cylindrical tube.

7. The clip of claim 6 wherein said second tube has a textured outer surface.

8. The clip of claim 6 wherein said second tube includes a third predetermined width less than said first predetermined width of said passage of said first tube and greater than said second width of said longitudinal slot of said first tube.

9. The clip of claim 6 wherein said first tube comprises an elastic material and said longitudinal slot is expandable for passage of said second tube therethrough and into said passage of said first tube.

10. The clip of claim 9 wherein said second tube includes a third channel having a second slot extending longitudinally therein and wherein said second tube comprises an elastic material and said second tube is compressible for passage through said longitudinal slot and into said passage of said first tube.

11. The clip of claim 10 wherein said first tube further comprises at least a projection extending from said wall of said first tube about said longitudinal slot thereof and at least partially into said passage of said first tube, said projection also extending into said third channel of said second tube when said second tube is positioned in said passage of said first tube.

12. The clip of claim 11 wherein said first tube includes at least one partially closed end.

13. The clip of claim 9 wherein said first tube includes at least one partially closed end.

14. The clip of claim 1 wherein said second channel includes a third opening in said outer wall.

15. The clip of claim 14 wherein said third opening of said second channel includes an opening communicating with said first opening.

16. The clip of claim 15 wherein at least one of said second and third openings includes a first predetermined height and a third predetermined width in said outer wall.

17. A surgical ligating clip comprising:

a first piece having an outer surface, a first preformed channel including a first opening in said outer surface, and a second preformed channel having a second opening isolated from direct communication with said first opening; and a second piece separate from said first piece and securably positionable in said first and second channel through said second opening, said first and said second channels being positioned in said first piece and forming with said second piece securely positioned in said first and second channels through said second opening a space in said first channel for ligation of a vessel at least partially surrounded by said first and said second pieces when the vessel is positioned in said first channel through said first opening.

18. The clip of claim 17 wherein said second channel communicates with said first channel and wherein said second opening is in said outer surface.

19. The clip of claim 17 wherein said second channel does not communicate with said first channel and wherein said second opening is in said outer surface.

20. A surgical ligating clip comprising:

a first, at least partially cylindrical, elastic material tube having a first outer wall, a first preformed channel including a first passage extending longitudinally in said first tube and having a first predetermined width, said first channel also including a first longitudinal slot in said first outer wall communicating with said first passage and having a second predetermined width less than said first width of said first passage, and a second channel including first and second openings communicating with and on opposite sides of said first slot, each of said openings having a predetermined height and width for insertion of a vessel in said second channel and through said outer wall, said first outer wall having projections extending from ends of said first outer wall adjacent said first slot and into said passage; and a second, at least partially cylindrical, elastic material tube separate from said first tube and having a third predetermined width greater than said second predetermined width of said first slot and less than said first predetermined width of said first passage of said first tube, a second outer wall, and a third channel including a second passage extending longitudinally in said second tube and a second longitudinal slot in said second outer wall for compression of said second tube and passage of said second tube through said first slot and into said first passage of said first tube, said second outer wall engaging said projections when said second tube is positioned in said first passage of said first tube.

21. A surgical ligating clip applicator comprising:

a housing having a first distal end, a vessel channel positioned proximate said first distal end and having a vessel access opening for communicating with an opening in a first, ligating clip piece when the first piece is positioned in said vessel channel, and a first piece passage communicating with said vessel channel for delivering a first piece to said vessel channel; and an insertion mechanism having a second distal end, a delivery position, a delivery passage positioned proximate said second distal end for communicating with a channel in a first piece when the first piece is positioned in said vessel channel and said insertion mechanism is positioned in said delivery position, a second piece passage communicating with said delivery passage for delivering a second piece to said delivery passage, and an insertion projection responsive to a force for moving said insertion projection into said delivery passage for engagement with a second, ligating clip piece separate from the first piece when the second piece is in said delivery passage and said insertion mechanism is in said delivery position and positioning the second piece from said delivery passage into a channel in the first piece through an opening in the first piece when the first piece is positioned in said vessel channel.

22. The applicator of claim 21 further comprising trigger means connected to said insertion mechanism and responsive to a force for positioning said insertion mechanism in said delivery position, moving said insertion projection into said delivery passage for engagement with a second piece when the second piece is in said delivery passage and said insertion mechanism is in said delivery position, and positioning the second piece from said delivery passage into the channel of the first piece through an opening in the first piece when the first piece is positioned in the vessel channel.

23. The applicator of claim 22 further comprising a clip ejector positioned in an ejector channel of said housing and having a relaxed position, an ejected position, and a distal end extending into said vessel channel when in said ejected position and a proximal end releasably connected to said trigger when in said ejected position.

24. The applicator of claim 23 further comprising a handle connected to said housing and including a grip, said trigger pivotedly connected to said grip, a first spring connected to said proximal end of said clip ejector for urging said clip ejector to said relaxed position.

25. The applicator of claim 24 wherein said handle includes a release mechanism engaging said proximal end of said clip ejector for releasing said clip ejector from said trigger when said clip ejector is in said ejected position.

26. The applicator of claim 24 wherein said handle includes a second spring connected to said grip and said trigger for urging said trigger into a released position.

27. The applicator of claim 21 wherein said housing further includes a guide channel extending longitudinally therein, wherein said insertion mechanism includes a carriage positioned within said guide channel of said housing, said carriage having an insertion projection channel extending longitudinally therein, and wherein said insertion projection is positioned in said insertion projection channel of said carriage.

28. The applicator of claim 27 wherein said insertion projection includes a push rod positioned in said insertion projection channel of said carriage and a clamping arm pivotedly connected to said push rod and responsive to a force for moving said clamping arm through said delivery passage.

29. The applicator of claim 28 wherein said carriage includes a deflection arm positioned proximate said delivery passage for guiding said clamping arm into said delivery passage of said carriage when said push rod is urged toward said second distal end of said carriage.

30. The applicator of claim 27 further comprising a handle connected to said housing and including a grip and a trigger pivotedly connected to said grip and said insertion mechanism.

31. The applicator of claim 30 wherein said trigger is also pivotedly connected to said insertion projection.

32. The applicator of claim 30 further comprising an outer sleeve having a passage extending longitudinally therein containing said housing, said carriage, and said insertion mechanism and connectable at a proximal end thereof to said handle.

33. The applicator of claim 21 wherein said housing further includes a first spring for communicating with a first piece when positioned in said first piece passage and urging the first piece toward said first distal end of said housing.

34. The applicator of claim 33 wherein said insertion mechanism includes a second spring for communicating with a second piece when the second piece is positioned in said second piece passage and urging the second piece toward said second distal end of said insertion mechanism.

35. The applicator of claim 33 further comprising a positioning projection for extending into said first piece passage of said housing and into an opening in a first piece when the first piece is positioned in said first piece passage.

36. The applicator of claim 21 further comprising a positioning projection extending from said first distal end and into said vessel channel for communicating with an opening in the first piece when the first piece is positioned in said vessel channel.

37. The applicator of claim 21 wherein said housing includes a stop positioned at said first distal end engaging said second distal end of said insertion mechanism when said insertion mechanism is in said delivery position.

38. A method of ligating a vessel utilizing the applicator of claim 21 comprising:
providing a first piece having an outer surface, a first preformed channel including a first opening in said outer surface, and a second preformed channel communicating with said first channel and including a second opening in said outer surface communicating with said first opening;
providing a second piece separate from said first piece;
positioning a vessel in at least one of said first and second channels of said first piece through at least one of said first and second openings in said outer surface of said first piece; and
securably positioning said second piece in at least one of said first and second channels through at least one of said first and second openings of said first piece.

39. The method of claim 38 wherein the step of positioning a vessel in at least one of said first and second channels includes positioning said first piece in said vessel channel of said applicator and positioning a vessel in said at least one of said first and second channels of said first piece through said vessel access opening of said housing.

40. The method of claim 39 wherein the step of securably positioning said second piece in said at least one of said first and second channels includes positioning said second piece in said delivery passage of said insertion mechanism, moving said insertion projection into said delivery passage and positioning said second piece from said delivery passage into said at least one of said first and second channels of said first piece through said at least one of said first and second openings.

41. A surgical ligating clip applicator comprising:
an outer sleeve having a passage extending longitudinally therethrough;
a housing positioned within said passage of said outer sleeve and having a first distal end, a clip ejector channel extending longitudinally therein, a first tube passage extending longitudinally therein and having a plurality of first tubes positioned therein, a first spring communicating with said plurality of first tubes urging said plurality of first tubes towards said first distal end and into a vessel access channel, a guide channel extending longitudinally therein, and a vessel access channel positioned transverse to and communicating with said first tube passage about said first distal end and having a vessel access opening communicating with first and second openings of a first tube positioned in said vessel access channel;

a carriage positioned within said guide channel of said housing and having a delivery position, a second distal end, a second tube passage extending longitudinally therein and having a plurality of second tubes positioned therein separated from said plurality of first tubes, a second spring urging said plurality of second tubes toward said second distal end and into said delivery passage, a delivery passage communicating with said second tube passage about said second distal end, having a second tube positioned therein and also communicating with a first slot and said first and second openings of said first tube in said vessel channel when said carriage is positioned in said delivery position about said first distal end of said housing, a deflection arm positioned proximate said delivery passage for guiding a clamping arm into said delivery passage when said carriage is positioned in said delivery position, and a push rod channel extending longitudinally therein;

a push rod positioned in said push rod channel of said carriage;

a clamping arm pivotedly connected to said push rod and responsive to a force for moving said clamping arm through said delivery passage when said carriage is in said delivery position and positioning said second tube into said first channel of said first tube through said first slot and engaging said second outer wall about said second slot of said second tube with said projections of said first tube;

a clip ejector positioned in said ejector channel of said housing and having a relaxed position, an ejected position, and a distal end extending into said vessel access channel when in said ejected position and a proximal end releasably connected to a trigger of said handle when in said ejected position; and a handle connected to said housing and said outer sleeve and including a grip; a trigger pivotedly connected to said grip, said carriage and said push rod; a third spring connected to said grip and said trigger and urging said trigger into said released position; a release mechanism engaging said proximal end of said clip ejector for releasing said ejector from said trigger when said clip ejector is in said ejected position; a fourth spring connected to said proximal end of said clip ejector urging said clip ejector to said relaxed position; and a fifth spring positioned between said trigger and said carriage relaxing said connection between said trigger and said carriage when in said delivery position.

42. A surgical ligating clip applicator comprising:
a housing having a first distal end; a vessel channel positioned proximate said first distal end and having a vessel access opening for communicating with a second channel extending through an outer wall of a first, ligating clip tube when the first tube is positioned in said vessel channel; and a first tube passage communicating with said vessel channel for delivering a first tube to said vessel channel; and an insertion mechanism having a second distal end, a delivery position, a delivery passage positioned proximate said second distal end for communicating with a first channel extending longitudinally in a first tube when the first tube is positioned in said vessel channel and said insertion mechanism is positioned in said delivery position about said first distal end of said housing, a second tube passage communicating with said delivery passage for delivering a second tube to said delivery passage, and an insertion projection responsive to a force for moving said insertion projection into said delivery passage when said insertion mechanism is in said delivery position and positioning a second tube separate from the first tube when in said delivery passage from said delivery passage and into the first channel of the first tube through a longitudinal slot in the outer wall of the first tube.

43. The applicator of claim 42 wherein said housing includes a guide channel extending longitudinally therein and wherein said insertion mechanism includes a carriage slidably positioned within said guide channel.

44. The applicator of claim 43 further comprising a trigger connected to said carriage and said insertion projection and responsive to a force for positioning said carriage in said delivery position, moving said insertion projection into said delivery passage for engagement with the second tube when the second tube is in said delivery passage and said carriage is in said delivery position, and positioning the second tube when positioned in said delivery passage from said delivery passage into the first channel of the first tube through the longitudinal slot in the outer wall of the first tube when the first tube is positioned in said vessel channel.

45. The applicator of claim 44 wherein said carriage includes an insertion projection channel extending longitudinally therein and wherein said insertion projection includes a push rod positioned in said insertion projection channel of said carriage and a clamping arm pivotedly connected to said push rod and responsive to said force for moving said clamping arm through said delivery passage.

46. The applicator of claim 45 wherein said carriage includes a deflection arm positioned proximate said delivery passage for guiding said clamping arm into said delivery passage of said carriage when said push rod is urged toward said second distal end of said carriage.

47. The applicator of claim 46 further comprising a handle connected to said housing and including a grip, said trigger pivotedly connected to said grip, and a first spring connected to said grip and said trigger urging said trigger into a released position.

48. The applicator of claim 47 further comprising a second spring positioned between said trigger and said carriage relaxing said connection between said trigger and said carriage when in said delivery position.

49. The applicator of claim 48 further comprising a clip ejector positioned in an ejector channel of said housing and having a relaxed position, an ejected position, and a distal end extending into said vessel channel when in said ejected position and a proximal end releasably connected to said trigger when said clip ejector is in said ejected position.

50. The applicator of claim 49 further comprising a third spring connected to said proximal end of said clip ejector urging said clip ejector to said relaxed position.

51. The applicator of claim 50 wherein said handle further includes a release mechanism engaging said proximal end of said clip ejector for releasing said clip ejector from said trigger when said clip ejector is in said ejected position.

52. The applicator of claim 51 wherein said housing includes a stop positioned at said first distal end engaging said second distal end of said carriage when said carriage is in said delivery position.

53. The applicator of claim 52 wherein said housing further includes a fourth spring for communicating with a first tube when positioned in said first tube passage and urging the first tube toward said distal end of said housing.

54. The applicator of claim 53 further comprising a positioning projection for extending into said first tube passage of said housing and into a first slot of a first tube when the first tube is positioned in said first tube passage.

55. The applicator of claim 54 wherein said carriage includes a fifth spring for communicating with a second tube when positioned in said second tube passage and urging the second tube toward said distal end of said carriage.

56. The applicator of claim 55 further comprising a second positioning projection for extending into said first or second tube passage of said carriage and into a second slot of a second tube when positioned in said second tube passage.

57. The applicator of claim 55 further comprising a third positioning projection for extending from said stop and into the first slot of the first tube when the first tube is positioned in said vessel channel.

58. The applicator of claim 57 further comprising an outer sleeve connected at a proximal end thereof to said handle and having a passage extending longitudinally therein; said passage containing said housing, said carriage, and said insertion mechanism.

59. A surgical ligating clip applicator comprising:
a housing having a first distal end, a vessel channel positioned proximate said first distal end and having a vessel across opening for communicating with an opening in an outer surface of a first, ligating clip piece when the first piece is positioned in said vessel channel, and a first piece passage communicating with said vessel channel for delivering a first piece to said vessel channel; and
an insertion mechanism having a second distal end, a delivery position, a delivery passage positioned proximate said second distal end for communicating with a channel in a first piece when the first piece is positioned in said vessel channel and said insertion mechanism is positioned in said delivery position, a second piece passage communicating with said delivery passage for delivering a second piece to said delivery passage, and an insertion projection responsive to a force for moving said insertion projection into said delivery passage for engagement with a second, ligating clip piece separate from the first piece when the second piece is in said delivery passage and said insertion mechanism is in said delivery position and positioning the second piece from said delivery passage into the channel of the first piece when the first piece is positioned in said vessel channel.

60. A method of ligating a vessel utilizing the applicator of claim 59 comprising:
providing a first piece having an outer surface, a first preformed channel including a first opening in said outer surface, and a second preformed channel;
providing a second piece separate from said first piece and securably positionable in at least one of said first and second channels;
positioning a vessel in said first channel through said first opening in said outer surface of said first piece; and
securably positioning said second piece in said at least one of said first and second channels.

61. The method of claim 60 wherein the step of positioning a vessel includes positioning said first piece in said vessel channel of said applicator and positioning the vessel in said first channel of said first piece and said vessel channel of said applicator.

62. The method of claim 61 wherein the step of securably positioning said second piece includes positioning said second piece in said delivery passage, moving said insertion projection into said delivery passage, and positioning said second piece from said delivery passage into said at least one of said first and second channels of said first piece of said clip.

63. A surgical ligating clip applicator comprising:
a housing having a first distal end, a vessel channel positioned proximate said first distal end and having a vessel access opening for communicating with an opening in an outer surface of a first, ligating clip piece when the first piece is positioned in said vessel channel, and a first piece passage communicating with said vessel channel for delivering a first piece to said vessel channel; and
an insertion mechanism having a second distal end, a delivery position, a delivery passage positioned proximate said second distal end for communicating with a preformed channel of the first piece when the first piece is positioned in said vessel channel and said insertion mechanism is positioned in said delivery position, a second piece passage communicating with said delivery passage for delivering a second piece to said delivery passage, and insertion projection means for engaging a second, ligating clip piece separate from the first piece when the second piece is in said delivery passage and said insertion mechanism is in said delivery position and positioning the second piece from said delivery passage into the preformed channel of the first piece.

64. A method of ligating a vessel utilizing the applicator of claim 63, comprising:
providing a first piece having an outer surface and a preformed channel including an opening in said outer surface;
providing a second piece separate from said first piece;
positioning a vessel in said preformed channel through said opening in said outer surface of said first piece; and
securably positioning said second piece in said channel.

65. The method of claim 64 wherein the step of positioning a vessel includes positioning said first piece in said vessel channel of said applicator and positioning a vessel in said preformed channel of said first piece positioned in said vessel channel of said applicator.

66. The method of claim 65 wherein the step of securably positioning said second piece includes positioning said second piece in said delivery passage, said insertion projection means engaging said second piece in said delivery passage and positioning said second piece into said preformed channel of said first piece.

* * * * *